United States Patent
Mizuhara

(10) Patent No.: US 9,619,023 B2
(45) Date of Patent: Apr. 11, 2017

(54) TERMINAL, SYSTEM, COMMUNICATION METHOD, AND RECORDING MEDIUM STORING A COMMUNICATION PROGRAM

(71) Applicant: Takuya Mizuhara, Kanagawa (JP)

(72) Inventor: Takuya Mizuhara, Kanagawa (JP)

(73) Assignee: RICOH COMPANY, LTD., Tokyo (JP)

( * ) Notice: Subject to any disclaimer, the term of this patent is extended or adjusted under 35 U.S.C. 154(b) by 0 days.

(21) Appl. No.: 14/996,324

(22) Filed: Jan. 15, 2016

(65) Prior Publication Data
US 2016/0252958 A1 Sep. 1, 2016

(30) Foreign Application Priority Data
Feb. 27, 2015 (JP) .................................. 2015-039021

(51) Int. Cl.
| | | |
|---|---|---|
| *G06F 3/13* | (2006.01) | |
| *G06F 3/01* | (2006.01) | |
| *H04N 7/14* | (2006.01) | |
| *G06F 19/00* | (2011.01) | |

(52) U.S. Cl.
CPC .......... *G06F 3/013* (2013.01); *G06F 19/3418* (2013.01); *H04N 7/147* (2013.01)

(58) Field of Classification Search
CPC .................................................. G06F 19/3418
USPC ........ 235/404; 345/156, 158, 419, 633, 672; 348/45, 66, 78, 143; 362/5; 382/108, 382/128, 195, 254; 600/437; 701/70; 702/94, 184; 715/863; 340/573; 351/205, 206; 356/29
See application file for complete search history.

(56) References Cited

U.S. PATENT DOCUMENTS

| | | | | |
|---|---|---|---|---|
| 5,661,519 A | * | 8/1997 | Franetzki | ........... A61B 1/00183 348/65 |
| 2004/0109135 A1 | * | 6/2004 | Watanabe | ............ A61B 3/1225 351/205 |
| 2004/0254763 A1 | * | 12/2004 | Sakai | ...................... H04L 67/12 702/184 |

(Continued)

FOREIGN PATENT DOCUMENTS

| | | |
|---|---|---|
| JP | 11-224152 | 8/1999 |
| JP | 2012-178135 | 9/2012 |

*Primary Examiner* — Gerald Gauthier
(74) *Attorney, Agent, or Firm* — Harnesss, Dickey & Pierce, P.L.C.

(57) ABSTRACT

A communication terminal for communicating with a counterpart communication terminal includes a receiver that receives image data including an eye image of a user operating the counterpart communication terminal from the counterpart communication terminal, the eye image of the user being captured at the counterpart communication terminal while the user is viewing a predetermined position on a counterpart display, and circuitry that specifies a sightline position indicating a sightline position of the user operating the counterpart communication terminal based on the received image data, generates calibration data indicating a relationship between a first area including the specified sightline position of the user and a second area including the predetermined position on the counterpart display, and adjusts the specified sightline position of the user on a display at the communication terminal based on the generated calibration data.

14 Claims, 18 Drawing Sheets

(56) References Cited

U.S. PATENT DOCUMENTS

| | | | |
|---|---|---|---|
| 2005/0195587 A1* | 9/2005 | Moctezuma De La Barrera | A61B 90/30 362/5 |
| 2005/0265619 A1* | 12/2005 | Ozaki | G06T 3/0018 382/254 |
| 2007/0229660 A1* | 10/2007 | Yamaguchi | H04N 7/181 348/143 |
| 2007/0230797 A1* | 10/2007 | Hisanaga | A61B 3/113 382/195 |
| 2007/0239005 A1* | 10/2007 | Ogasawara | A61B 8/14 600/437 |
| 2009/0069994 A1* | 3/2009 | Uechi | B60T 7/22 701/70 |
| 2009/0216476 A1* | 8/2009 | Hofmann | G01C 15/00 702/94 |
| 2009/0237644 A1* | 9/2009 | Uechi | B60W 30/10 356/29 |
| 2010/0134519 A1* | 6/2010 | Yamada | G06T 11/00 345/672 |
| 2010/0185990 A1* | 7/2010 | Ha | G06F 3/01 715/863 |
| 2010/0315415 A1* | 12/2010 | Asami | A63B 24/0003 345/419 |
| 2011/0299746 A1* | 12/2011 | Kobayashi | A61B 6/466 382/128 |
| 2013/0021336 A1* | 1/2013 | Tsukagoshi | G02B 27/2214 345/419 |
| 2013/0188841 A1* | 7/2013 | Pollock | G01C 11/02 382/108 |
| 2014/0043229 A1* | 2/2014 | Higaki | G06F 3/013 345/156 |
| 2014/0098091 A1* | 4/2014 | Hori | G06T 7/602 345/419 |
| 2015/0034722 A1* | 2/2015 | Roman | F41G 3/06 235/404 |
| 2015/0116201 A1* | 4/2015 | Tsou | G06F 3/013 345/156 |
| 2015/0123997 A1* | 5/2015 | Hayasaka | G02B 27/017 345/633 |
| 2015/0190038 A1* | 7/2015 | Sakuragi | A61B 1/00009 348/45 |
| 2015/0199812 A1* | 7/2015 | Hakoshima | A61B 3/113 348/78 |
| 2015/0227197 A1* | 8/2015 | Nomura | G06F 3/005 345/156 |
| 2015/0227789 A1* | 8/2015 | Watanabe | G06K 9/00255 348/78 |
| 2015/0301598 A1* | 10/2015 | Itoh | G06F 3/013 345/158 |
| 2016/0070345 A1* | 3/2016 | Huang | G06F 3/01 351/206 |
| 2016/0139433 A1* | 5/2016 | Du | G02B 27/017 351/205 |
| 2016/0180692 A1* | 6/2016 | Du | G02B 27/017 340/573.1 |
| 2016/0210432 A1* | 7/2016 | Mizuhara | G06F 19/3418 |
| 2016/0231809 A1* | 8/2016 | Yasuda | G09G 5/00 |

* cited by examiner

FIG. 3

MEDICAL CHECKUP DATA

| NAME | SEX | AGE |
|---|---|---|
| TARO RICOH | MALE | 36 |

| CHECKED ITEMS | 2014/05/01 | 2013/05/01 | 2012/05/01 | 2011/05/01 |
|---|---|---|---|---|
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| ERYTH-ROCYTE | 481 | 472 | 491 | 456 |
| NEUTRAL FAT | 172 | 178 | 173 | 167 |

| PAST MEDICAL HISTORY | ANSWERS |
|---|---|
| HIGH-BLOOD PRESSURE | YES |
| STROKE | NO |
| CANCER | NO |
| DIABETES | YES |
| ARRHYTHMIA | NO |
| BRONCHIAL ASTHMA | NO |

| LIFESTYLE HABITS | ANSWERS |
|---|---|
| EXERCISE HABIT | ONCE A WEEK |
| SMOKING | MORE THAN 10 PIECES A WEEK |
| DRINKING | 1 LITTER A WEEK |
| SLEEPING TIME | 6 HOURS (AVE) |
| EAT FRIED FOODS | YES |
| CONSTIPATION | NO |
| FEEL STRESSED | NO |

FIG. 4

MEDICAL CHECKUP DATA

| NAME | SEX | AGE |
|---|---|---|
| TARO RICOH | MALE | 36 |

| CHECKED ITEMS | 2014/05/01 | 2013/05/01 | 2012/05/01 | 2011/05/01 |
|---|---|---|---|---|
| HEIGHT | 170.5 | 170.4 | 170.6 | 170.8 |
| WEIGHT | 70.4 | 69.1 | 66.1 | 65.3 |
| BMI | 24.2 | 23.8 | 22.8 | 22.4 |
| BLOOD PRESSURE | 130 | 111 | 126 | 132 |
| URIC ACID | 6.4 | 6.5 | 6.8 | 6.1 |
| ERYTHROCYTE | 481 | 472 | 491 | 456 |
| NEUTRAL FAT | 172 | 178 | 173 | 167 |

OBSERVING POINT MARKER ∨

RECEIVING USER'S IMAGE DATA

| PAST MEDICAL HISTORY | ANSWERS |
|---|---|
| HIGH-BLOOD PRESSURE | YES |
| STROKE | NO |
| CANCER | NO |
| DIABETES | YES |
| ARRHYTHMIA | NO |
| BRONCHIAL ASTHMA | NO |

| LIFESTYLE HABITS | ANSWERS |
|---|---|
| EXERCISE HABIT | ONCE A WEEK |
| SMOKING | MORE THAN 10 PIECES A WEEK |
| DRINKING | 1 LITTER A WEEK |
| SLEEPING TIME | 6 HOURS (AVE) |
| EAT FRIED FOODS | YES |
| CONSTIPATION | NO |
| FEEL STRESSED | NO |

DISPLAY OBSERVING POINT MARKER

| USER ID | NAME | SEX | AGE | CALIBRATION DATA |
|---|---|---|---|---|
| 123456 | TARO RICOH | MALE | 36 | (−1, 0) |
| 123457 | HANAKO PENTA | FEMALE | 35 | (0, +1) |
| ⋮ | ⋮ | ⋮ | ⋮ | ⋮ |

FIG. 8A

| USER ID | CHECKED ITEMS | 2014/05/01 | 2013/05/01 | 2012/05/01 | 2011/05/01 |
|---|---|---|---|---|---|
| 12345 | HEIGHT | 170.5 | 170.4 | 170.6 | 170.8 |
| | WEIGHT | 70.0 | 69.1 | 66.1 | 65.3 |
| | BMI | 24.2 | 23.8 | 22.8 | 22.4 |
| | BLOOD PRESSURE | 130 | 111 | 126 | 132 |
| | URIC ACID | 6.4 | 6.5 | 6.8 | 6.1 |
| | ERYTHROCYTE | 481 | 472 | 491 | 456 |
| | NEUTRAL FAT | 172 | 178 | 173 | 167 |

FIG. 8B

| USER ID | PAST MEDICAL HISTORY | ANSWERS |
|---|---|---|
| 12345 | HIGH-BLOOD PRESSURE | YES |
| | STROKE | NO |
| | CANCER | NO |
| | DIABETES | YES |
| | ARRHYTHMIA | NO |
| | BRONCHIAL ASTHMA | NO |

FIG. 8C

| USER ID | LIFESTYLE HABITS | ANSWERS |
|---|---|---|
| 12345 | EXERCISE HABIT | ONCE A WEEK |
| | SMOKING | MORE THAN 10 PIECES A WEEK |
| | DRINKING | 1 LITTER A WEEK |
| | SLEEPING TIME | 6 HOURS (AVE) |
| | EAT FRIED FOODS | YES |
| | CONSTIPATION | NO |
| | FEEL STRESSED | NO |

| PUPIL·CORNEAL REFLEX | DISPLAY AREAS |
|---|---|
| (1, −1) | DISPLAY AREA s1 (UPPER LEFT) |
| (−1, −1) | DISPLAY AREA s2 (UPPER RIGHT) |
| (1, 1) | DISPLAY AREA s3 (LOWER LEFT) |
| (−1, 1) | DISPLAY AREA s4 (LOWER RIGHT) |

|  | DISPLAY AREA s1 | DISPLAY AREA s2 | DISPLAY AREA s3 | DISPLAY AREA s4 |
|---|---|---|---|---|
| DISPLAY POSITION OF POINTING MARKER | (20, 40) | (1200, 50) | (100, 880) | (1150, 900) |
| DISPLAY POSITION OF CALIBRATED MARKER | (320, 240) | (960, 240) | (320, 720) | (960, 720) |
| COMPARISON RESULTS | (−1, 0) | (−1, 0) | (0, 0) | (−1, 0) |
| COMPARISON STATUS | 1 | 0 | 0 | 0 |

TERMINAL, SYSTEM, COMMUNICATION METHOD, AND RECORDING MEDIUM STORING A COMMUNICATION PROGRAM

CROSS-REFERENCE TO RELATED APPLICATIONS

This patent application is based on and claims priority pursuant to 35 U.S.C. §119(a) to Japanese Patent Application No. 2015-039021, filed on Feb. 27, 2015 in the Japan Patent Office, the entire disclosures of which are hereby incorporated by reference herein.

BACKGROUND

Technical Field

The present invention relates to a terminal, a system, a communication method, and a non-transitory recording medium storing a communication program.

Background Art

Recently, videoconference systems for allowing a user to communicate with a counterpart at a remotely-located site via the Internet have been widely used. Since the videoconference systems allow the user to have conversation while watching a face of the counterpart, the user feels as he or she were having a face-to-face conversation with the counterpart locally.

It has become difficult to allocate industrial physicians to all offices from a viewpoint of labor cost. To cope with this issue, some industrial physicians use the videoconference systems to examine a patient at a remotely-located site.

SUMMARY

An example embodiment of the present invention provides a novel communication terminal for communicating with a counterpart communication terminal that includes a receiver that receives image data including an eye image of a user operating the counterpart communication terminal from the counterpart communication terminal, the eye image of the user being captured at the counterpart communication terminal while the user is viewing a predetermined position on a counterpart display, and circuitry that specifies a sightline position indicating a sightline position of the user operating the counterpart communication terminal based on the received image data, generates calibration data indicating a relationship between a first area including the specified sightline position of the user and a second area including the predetermined position on the counterpart display, and adjusts the specified sightline position of the user on a display at the communication terminal based on the generated calibration data.

Further embodiments of the present invention provide a remote communication system, a communication method, and a non-transitory recording medium storing a communication program.

BRIEF DESCRIPTION OF THE DRAWINGS

A more complete appreciation of the disclosure and many of the attendant advantages and features thereof can be readily obtained and understood from the following detailed description with reference to the accompanying drawings, wherein:

FIG. 3 is a diagram illustrating an employee-side screen as an embodiment of the present invention;

FIG. 4 is a diagram illustrating an industrial-physician-side screen as an embodiment of the present invention;

FIG. 8A is a diagram illustrating a checkup result management table; FIG. 8B is a diagram illustrating a past medical history management table; FIG. 8C is a diagram illustrating a lifestyle habits management table;

Figure 1:
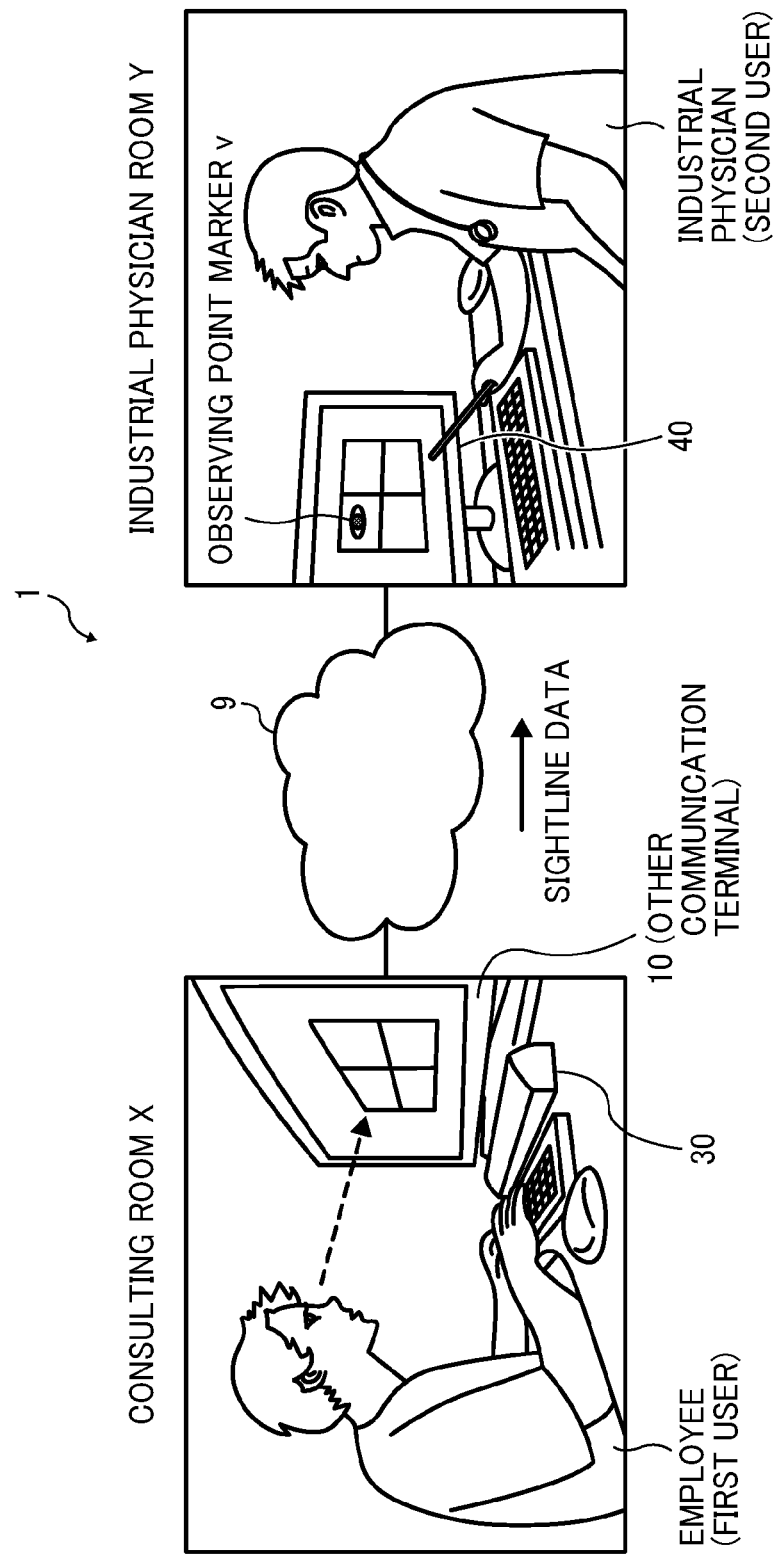
FIG. 1 is a schematic diagram illustrating a configuration of a consultation system as an embodiment of the present invention.

The accompanying drawings are intended to depict example embodiments of the present invention and should not be interpreted to limit the scope thereof. The accompanying drawings are not to be considered as drawn to scale unless explicitly noted.

DETAILED DESCRIPTION

The terminology used herein is for the purpose of describing particular embodiments only and is not intended to be limiting of the present invention. As used herein, the singular forms "a", "an" and "the" are intended to include the plural forms as well, unless the context clearly indicates otherwise. It will be further understood that the terms "includes" and/or "including", when used in this specification, specify the presence of stated features, integers, steps, operations, elements, and/or components, but do not preclude the presence or addition of one or more other features, integers, steps, operations, elements, components, and/or groups thereof.

In describing preferred embodiments illustrated in the drawings, specific terminology is employed for the sake of clarity. However, the disclosure of this patent specification is not intended to be limited to the specific terminology so selected, and it is to be understood that each specific element includes all technical equivalents that have the same function, operate in a similar manner, and achieve a similar result.

Referring to FIGS. 1 to 4, an embodiment of the present invention is described. FIG. 1 is a schematic diagram illustrating a configuration of a consultation system 1 according to the embodiment.

As shown in FIG. 1, the consultation system 1 in this embodiment includes an employee-side communication terminal 10, an employee-side sightline detection device 30, and an industrial-physician-side communication terminal 40. The communication terminal 10 and the sightline detection device 30 are located at a consultation room X where an employee visits for consultation with an industrial physician. The sightline detection device 30 is connected to the communication terminal 10 via a cable for transferring image data including at least an image of an eye of the employee. The communication terminal 40 is located at an industrial physician's room Y where the industrial physician works.

In this embodiment, general-purpose personal computers (PCs) are used for the communication terminals 10 and 40, and they are connected with each other communicably via a communication network 9 such as the Internet and a local area network (LAN).

It should be noted that any one of the communication terminals 10 and 40 may be implemented by a smartphone or a tablet device. Furthermore, at least the communication terminal 10 may be a terminal with a build-in sightline detection device 30, such that the communication terminal 10 may be dedicated to the remote consultation. In this disclosure, the communication terminal 10 may be referred to as a first communication terminal, or a counterpart communication terminal from a viewpoint of the communication terminal 40. The communication terminal 40 may be referred to as a second communication terminal.

For example, in FIG. 1, the consultation system 1 is used by the employee as an example of the first user, and the industrial physician as an example of the second user. The other example combinations of the first user and the second user include a corporate manager as the first user and the industrial physician as the second user, or the employee or the corporate manager as the first user and any other physician, a nurse, or a pharmacist as the second user. The other example combinations of the first user and the second user further include a teacher or an instructor as the first user and a student of any age or a guardian of the student as the second user. Furthermore, the other example combinations of the first user and the second user include a subordinate as the first user and a boss as the second user.

In FIG. 1, the sightline detection device 30 transfers image data acquired by capturing at least the employee's eye part to the communication terminal 10, and the communication terminal 10 transfers the image data to the communication terminal 40. Subsequently, the communication terminal 40 displays an observing point marker v based on the employee's sightline direction based on the image data. In this case, an eyeball-shaped marker is displayed as an example of the observing point marker v. As a result, even in case of having a remote consultation with the employee, the industrial physician can perceive, from the unstable sightline, that the employee has some concerns or seems to be depressed, just like the face-to-face consultation.

It should be noted that the observing point marker v indicating the employee's sightline direction is not displayed on the communication terminal 10. This is because the industrial physician cannot determine whether or not the employee is in a depression etc. precisely if the employee recognizes his/her own observing point marker v. In addition, the observing point marker v is an example of observing point information. Other examples of the observing point information include not displaying the marker but modifying color of texts or width of frames etc. displayed as the medical checkup data (described later).

Figure 2:
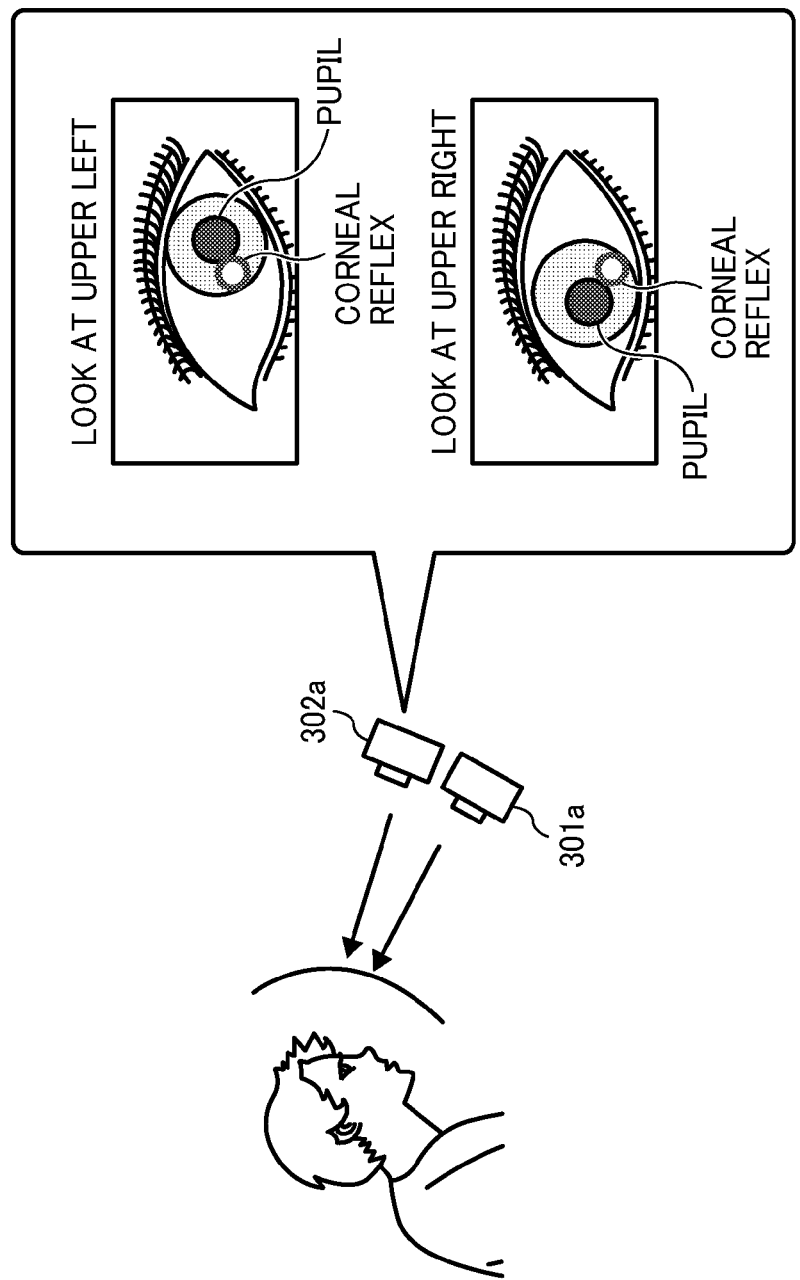
FIG. 2 is a schematic diagram illustrating a sightline detection method as an embodiment of the present invention.

Next, an outline of a sightline detection method is described below. FIG. 2 is a schematic diagram illustrating operation of detecting a sightline of the employee in this embodiment. The sightline detection method detects movements of the user's eyeballs to determine directions at which the user is looking. To start detecting movements of the user's eyeballs, firstly, a static part (reference point) and a movable part (moving point) of the user's eyes are detected at the detection device. After detecting the reference point and the moving point, the detection device detects the sightline of the user based on a position of the moving point in accordance with the reference point. There are various sightline detection methods, each of which differs in how the reference point and the moving point are each chosen. Among them, as a typical method, a corneal reflex sightline detection method in which corneal reflex is regarded as the reference point and the pupil is regarded as the moving point to analyze their positional relationship is described below.

In general, the detection device for performing the sightline detection method has an infrared light emitting diode (LED) lighting device 301a, which illuminates the user's face, and determines a position of reflected light of the emitted light on the cornea (the corneal reflex) as the reference point. The detection device further has an infrared camera 302a, which detects the user's sightline based on the position of the pupil with reference to the position of the corneal reflex. For example, as shown in FIG. 2, if the pupil of the left eye is located at upper left compared to the position of the corneal reflex, it is detected that the user is looking at upper left. By contrast, if the pupil of the left eye is located at upper right compared to the position of the corneal reflex, it is detected that the user is looking at upper right. The detected sightline data is expressed as coordinate data.

In this embodiment, the sightline detection method described above is applied to detect the first user's sightline during remote consultation, which is performed by the terminal 10 at the employee side in cooperation with the terminal 40 at the industrial physician side. As a result, in this embodiment, a screen shown in FIG. 3 is displayed on the communication terminal 10 on the employee side, and a screen shown in FIG. 4 is displayed on the communication terminal 40 on the industrial physician side.

Other examples of the sightline detection methods are an iris detection method using LMedS and an active appearance model (AAM) method etc. In the corneal reflex method, the iris detection method, and the AAM method, the sightline is detected based on image data indicating an image of a user. In the corneal reflex method, the coordinate data is output as the sightline data. By contrast, in the iris detection method and the AAM method, specific parameters are output as the sightline data. More specifically, in the iris detection method, an iris part of the user's eye is detected based on the image in which the user is captured, an ellipse is fit into the detected iris, and the sightline is detected based on three parameters, slope of the fit ellipse, major axis of the fit ellipse, and minor axis of the fit ellipse. In the AAM method, a face model is generated based on face images captured when the user faces into various directions, and the sightline is detected by storing (or learning) parameters of amount of characteristics acquired by associating the face models with the sightline directions.

FIG. 3 is a diagram illustrating an employee-side screen in this embodiment. FIG. 4 is a diagram illustrating an industrial-physician-side screen in this embodiment. As shown in FIG. 3, the communication terminal 10 displays a medical checkup data screen 1000 on a display 217 (described later). On the medical checkup data screen 1000, an employee's personal information display area 1010, a checkup result display area 1020, a medical history display area 1030, and a lifestyle habit display area 1040 are displayed. On the personal information display area 1010, the user's personal data such as employee name etc. is displayed. The medical checkup management data such as checkup results of the user's medical checkup etc. is displayed on the checkup result display area 1020, the medical history display area 1030, and the lifestyle habit display area 1040. That is, the user personal data and the medical checkup management data, which may be collectively referred to as the medical checkup data, is displayed as the content of the medical checkup data screen 1000. In this embodiment, the remote consultation is used for medical use. However, the purpose of the remote consultation is not limited to that. That is, it is possible to use the remote consultation for business use. As a result, the medical checkup data in this embodiment is an example of the user related data that indicates content related to the user. Other examples of the user related data are a performance result in an example case of a manager as the second user and a staff as the first user, a grade report or an examination sheet in an example case of a teacher as the second user and a student as the first user, an evidential photo or a questioning sheet in an example case of a detective as the second user and a suspect as the first user, and a fortune-telling result or an image of a palm in an example case of a fortune-teller as the second user and a customer as the first user.

By contrast, the communication terminal 40 displays a medical checkup data screen 4000 on a display 217 (described later). On the medical checkup data screen 4000, just like the screen of FIG. 3, a user's personal information display area 4010, a checkup result display area 4020, a medical history display area 4030, and a lifestyle habit display area 4040 are displayed. The user's personal information display area 4010, the checkup result display area 4020, the medical history display area 4030, and the lifestyle habit display area 4040 respectively display the same content as the corresponding user's personal information display area 1010, checkup result display area 1020, medical history display area 1030, and lifestyle habit display area 1040. The medical checkup data screen 4000 additionally displays an observing point marker v, a reception status display area 4110, and an observing point marker display button 4210. On the reception status display area 4110, a message indicating that the communication terminal 40 is receiving image data from the communication counterpart (i.e., the employee) is displayed. In this case, the message "receiving user's image data" is displayed as an example of the message. The observing point marker display button 4210 is a key pressed by the industrial physician to display the observing point marker v on the display 217 at the communication terminal 40. That is, the observing point marker display button 4210 accepts a command to display the observing point marker v from the industrial physician. It should be noted that the displayed position of the observing point marker v on the medical checkup data screen 4000 changes to reflect the employee's sightline direction that is currently detected.

Figure 5:
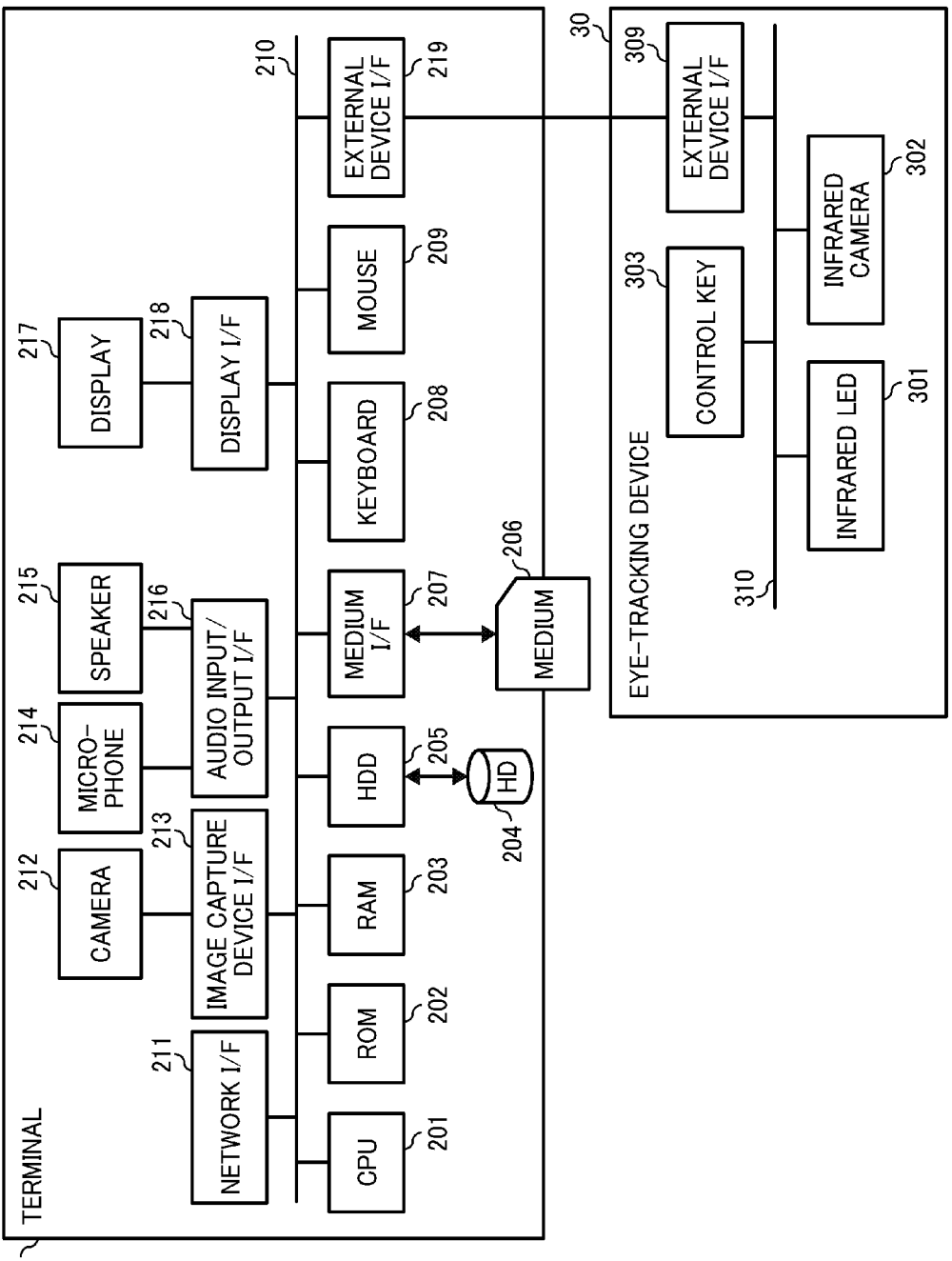
FIG. 5 is a diagram illustrating a hardware configuration of a communication terminal and a sightline detection device of the consultation system of FIG. 1 as the embodiment of the present invention.

Next, a hardware configuration of the communication terminals 10 and 40 and the sightline detection device 30 is described below with reference to FIG. 5. FIG. 5 is a diagram illustrating a hardware configuration of the communication terminal 10 and the sightline detection device 30 in this embodiment. Here, the communication terminal 40 has the same configuration as that of the communication terminal 10. Therefore, description of the communication terminal 40 is omitted, and the hardware configuration of the communication terminal 10 and the sightline detection device 30 is described below.

As shown in FIG. 5, the communication terminal 10 includes a central processing unit (CPU) 201, a read only memory (ROM) 202, a random access memory (RAM) 203, a hard disk (HD) 204, a hard disk drive (HDD) 205, a medium interface (I/F) 207, a keyboard 208, and a mouse 209.

Among those components, the CPU 201 controls entire operation of the communication terminal 10. The ROM 202 stores programs such as IPL etc. used for executing the CPU 201. The RAM 203 is used as a work area for the CPU 201. The HD 204 stores various data such as programs. The HDD 205 controls reading various data from the HD 204 and writing various data in the HD 204 under control of the CPU 201. The medium I/F 207 controls reading data from a recording medium such as a flash memory etc. and writing data in the recording medium 206. The keyboard 208 is an input device including multiple keys for inputting text, values, and various commands. The mouse 209 is an input device used for selecting or executing various commands, selecting a target to be processed, and moving a cursor etc.

In addition, the communication terminal 10 includes a network I/F 211, a camera 212, an image capture device I/F 213, a microphone 214, a speaker 215, an audio input/output I/F 216, a display 217, a display I/F 218, and an external device I/F 219.

Among those components, the network I/F 211 is an interface for transferring data via the communication network 9, such as a network interface card. The camera 212 captures a target object under control of the CPU 201 and outputs image data of the captured image. The image capture device I/F 213 is a circuit for controlling driving the camera 212. The microphone 214 is a built-in microphone for inputting audio such as audio of user's voice. The speaker 215 is a built-in speaker for outputting audio such as audio of the counterpart user's voice. The audio input/output I/F 216 is a circuit for processing input of an audio signal from the microphone 214 and output an audio signal to the speaker 215 under control of the CPU 201. The display 217 displays various information such as a cursor, a menu, a window, a text, a marker, and an image etc. The display I/F 218 outputs video (a still image and/or a movie) to the display 217 under control of the CPU 201. The external device I/F 219 is an interface for transferring data via a Universal Serial Bus (USB) cable etc.

Furthermore, the communication terminal 10 includes a bus line 210 such as an address bus and a data bus etc. for electrically connecting the components such as the CPU 201 described above with each other as shown in FIG. 5.

The programs described above may be stored as installable or executable files in a computer-readable recording medium such as the recording medium 206 described above for distribution. Alternatively, the programs described above may be stored not in the HD 204 but in the ROM 202. Other examples of the above-described recording medium include, but not limited to, a Compact Disc Recordable (CD-R), a Digital Versatile Disc (DVD), and a Blu-ray disc.

As shown in FIG. 5, the sightline detection device 30 includes an infrared LED lighting device 301, an infrared camera 302, a control key 303, an external device I/F 309, and a bus line 310.

Among those components, the infrared LED lighting device 301 is a lighting device including a diode that emits infrared light. The infrared camera 302 senses infrared. The external device I/F 309 is an interface for transferring data via a USB cable etc. The bus line 310 is a bus such as an address bus and a data bus etc. for electrically connecting the components such as the infrared LED lighting device 301 etc. described above with each other as shown in FIG. 5.

Figure 6:
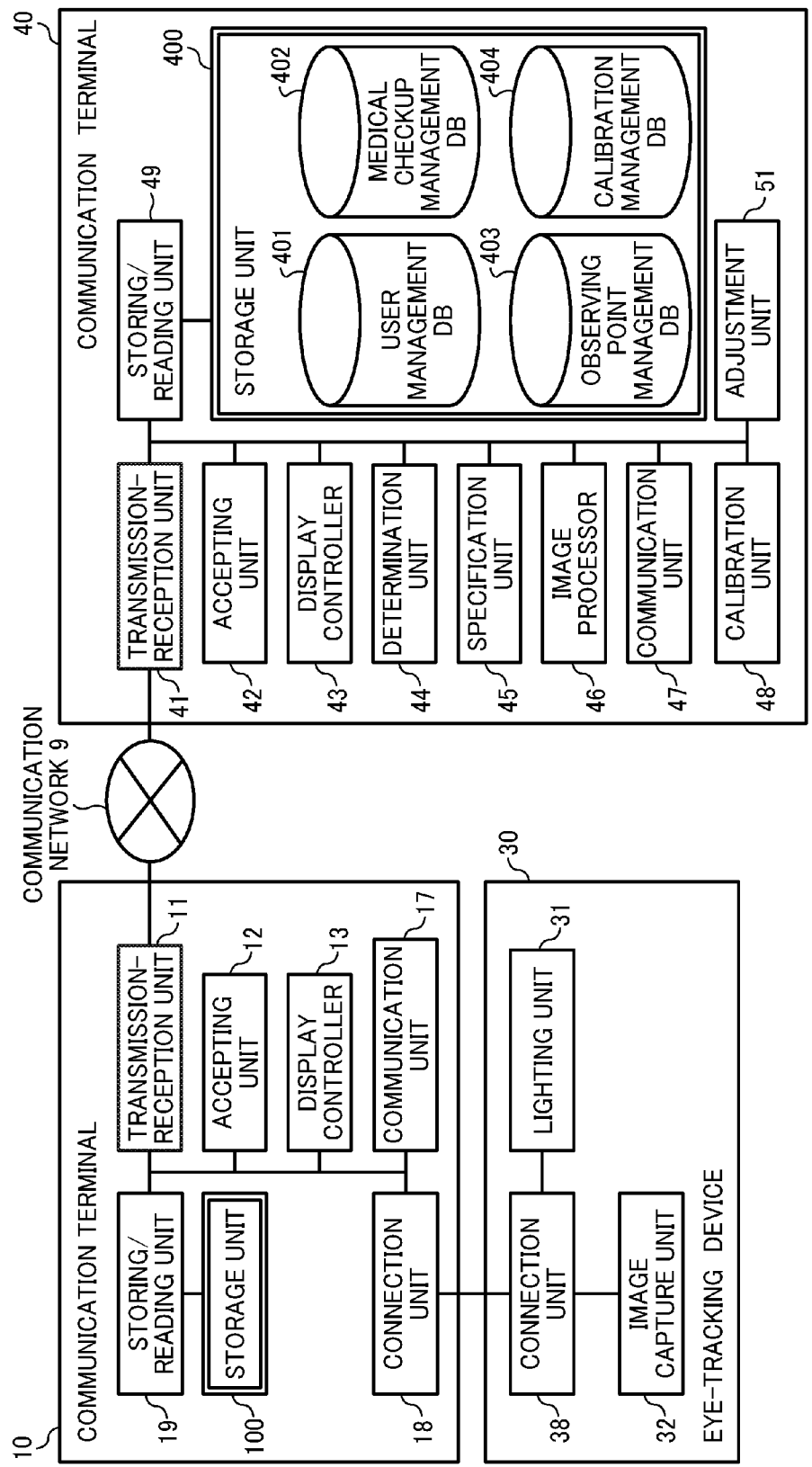
FIG. 6 is a diagram illustrating a functional configuration of the consultation system of FIG. 1.

Next, a functional configuration of the consultation system 1 in this embodiment is described below with reference to FIGS. 5 and 6. FIG. 6 is a diagram illustrating a functional configuration of the consultation system 1 in this embodiment.

As shown in FIG. 6, the communication terminal 10 includes a transmission-reception unit 11, an accepting unit 12, a display controller 13, a generator 14, a communication unit 17, a connection unit 18, and a storing/reading unit 19. Those components described above are functions or units implemented by operating some of the hardware components shown in FIG. 5 under control of the CPU 201 in accordance with programs expanded in the RAM 203 from the HD 204. In addition, the communication terminal 10 includes a storage unit 100 that may be implemented by the ROM 202, the RAM 203, and/or the HD 204 shown in FIG. 5.

The transmission-reception unit 11 in the communication terminal 10 is mainly implemented by processes performed by the network I/F 210 and the CPU 201 shown in FIG. 5. Mainly, the transmission-reception unit 11 transfers various data to the communication terminal 40 or receives various data from the communication terminal 40 via the communication network 9. For example, every time the infrared camera 302 captures an image of the employee at a predetermined interval, the transmission-reception unit 11 transmits sightline data indicating an employee's sightline direction.

The accepting unit 12 is mainly implemented by processes performed by the keyboard 208, the mouse 209, and the CPU 201 and accepts various selection, designation, or commands etc. by user operation.

The display controller 13 is mainly implemented by processes performed by the display I/F 218 and the CPU 201 and controls displaying various images and text on the display 217.

The generator generates sightline data based on image data including an image of the employee's eye acquired by an image capture unit 32 (described later). For example, in case of using the corneal reflex method described above is used, the sightline data is expressed as coordinate data.

The communication unit 17 is mainly implemented by processes performed by the camera 212, the image capture device I/F 213, the microphone 214, the speaker 215, the audio input/output I/F 216, the display 217, the display I/F 218, and the CPU 201 and communicates audio and video to the counterpart communication terminal 40 to carry out communication between the communication terminals 10 and 40.

The connection unit 18, which is mainly implemented by processes performed by the external device I/F 209 and the CPU 201, detects a connection to an external device, and communicates with the external device that is connected.

The storing/reading unit 19 stores various data in the storage unit 100 and reads various data from the storage unit 100.

As shown in FIG. 6, the sightline detection device 30 includes a lighting unit 31, an image capture unit 32, and a connection unit 38. Those components described above are functions or units implemented by operating some of the hardware components in the sightline detection unit 30 shown in FIG. 5.

The lighting unit 31 is implemented by operations of the infrared LED lighting device 301 and illuminates the user face by emitting infrared light.

The image capture unit 32 is implemented by operations of the infrared camera 302 as an example of the image capture unit and captures reflected light of the infrared emitted by the lighting unit 31 to generate image data.

The connection unit 38, which is mainly implemented by processes performed by the external device I/F 309, detects a connection to an external device and communicates with the external device that is connected.

As shown in FIG. 6, the communication terminal 40 includes a transmission-reception unit 41, an accepting unit 42, a display controller 43, a determination unit 44, a specification unit 45, an image processor 46, a communication unit 47, a calibration unit 48, a storing/reading unit 49, and an adjustment unit 51. Those components described above are functions or units implemented by operating some of the hardware components shown in FIG. 5 under control of the CPU 201 in accordance with programs expanded in the RAM 203 from the HD 204. In addition, the communication terminal 40 includes a storage unit 400 that may be implemented by the ROM 202, the RAM 203, and/or the HD 204 shown in FIG. 5. The storage unit 400 stores therein a user management database (DB) 401 that consists of a user management table. The storage unit 400 further stores a medical checkup management DB 402 that consists of a checkup result management table, a medical history management table, and a lifestyle habit management table. Furthermore, the storage unit 400 stores an observing point position management DB 403 that consists of an observing point position management table. In addition, the storage unit 400 stores a calibration management DB 404 that consists of a calibration management table.

It should be noted that the user management table stores various data to be used as the contents of user personal data. The checkup result management table, the medical history management table, and the lifestyle habit management table together store various data to be used as the contents of the medical checkup management data. That is, in FIGS. 3 and 4, the user management table has contents to be displayed in the user personal information display area 1010 (4010), the checkup result management table has contents to be displayed in the checkup result display area 1020 (4020), the medical history management table has contents to be displayed in the medical history display area 1030 (4030), and the lifestyle habit management table has contents to be displayed in the lifestyle habit display area 1040 (4040).

Figures 7A, 7B:
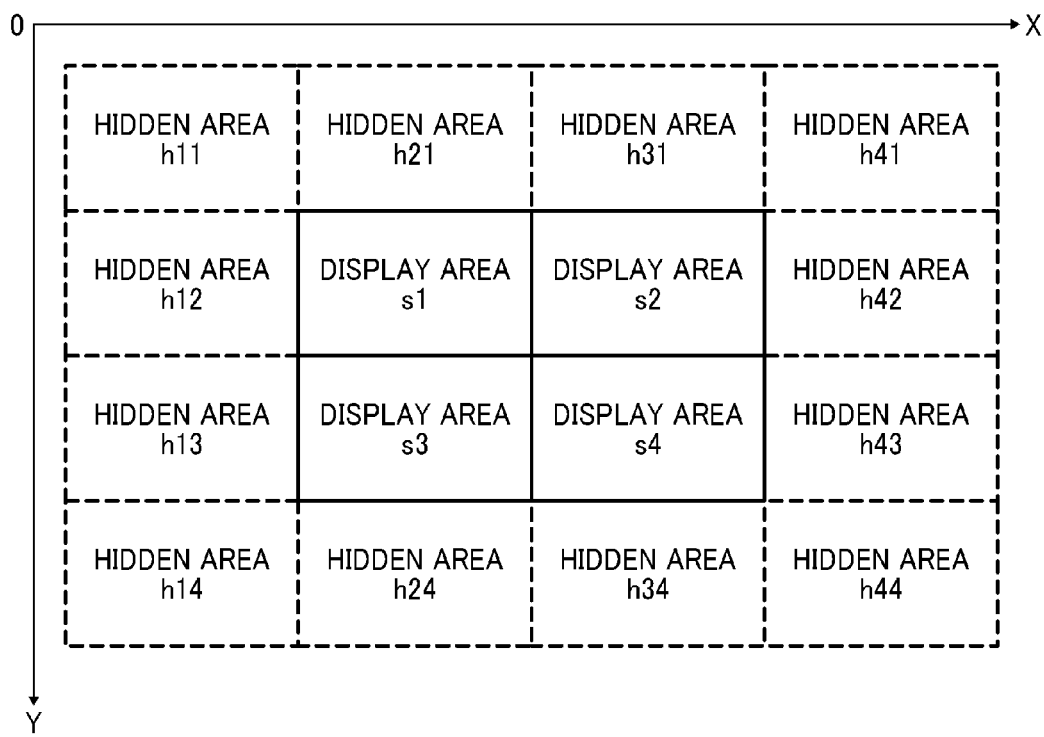
FIG. 7A is a conceptual diagram illustrating a user management table.
FIG. 7B is a conceptual diagram illustrating a display area including a user sightline position.

FIG. 7A is a conceptual diagram illustrating a user management table, and FIG. 7B is a conceptual diagram illustrating a display area including a user sightline position. The user management table, which is used to manage user personal information, stores, for each user, a user ID for identifying the user, a user name, a user sex, a user age, and calibration data indicating a calibration result associated with one another. Among multiple display areas illustrated in FIG. 7B, four display areas s1, s2, s3, and s4 in the center part indicate display areas that the medical checkup data screen 4000 on the industrial-physician side is divided into four display areas. In addition, twelve display areas (hidden areas h11, h21, h31, h41, h12, h42, h13, h43, h14, h24, h34, and h44) in the surrounding part indicate virtual display areas that are not displayed actually at the outer side of the medical checkup data screen 4000 on the industrial-physician side. It should be noted that the user ID is an example of user identification information for uniquely identifying a user. Examples of the user identification information include an employee number, a student number, and a social security number, which may be managed using the computerized personal data system. The number of display areas in the center part is not limited to four. For example, the number of display areas in the center part may be one, two, six, or more than eight. That is, the number of display areas in the surrounding part may be increased or decreased.

FIG. 8A is a conceptual diagram illustrating the checkup result management table. The checkup result management table stores a plurality of checkup items and past checkup dates for each check item in association with the user ID. Examples of the checked items include height, weight, Body Mass Index (BMI), blood pressure, uric acid, erythrocyte, and neutral fat.

FIG. 8B is a conceptual diagram illustrating the medical history management table. The medical history checkup table stores a plurality of past medical history items and user answers to questions regarding the past medical history items, in association with the user ID. Examples of the past medical history items include high-blood pressure, stroke, cancer, diabetes, arrhythmia, and bronchial asthma. If the answer is "yes", that indicates that the user has been diagnosed as having that disease, and if the answer is "no", that indicates that the user has not been diagnosed as having that disease.

FIG. 8C is a conceptual diagram illustrating the lifestyle habits management table. The lifestyle habit management table stores a plurality of lifestyle habit items and user's answers to questions of lifestyle habits in association with the user ID. Examples of the lifestyle habit items include exercise habit, smoking, drinking, sleeping time, eating many fried foods, constipation, and feeling stressed. If the answer is "yes", that indicates that the user practices the lifestyle habit item, and if the answer is "no", that indicates that the user does not practice the lifestyle habit item.

Figures 9, 10A, 10B:
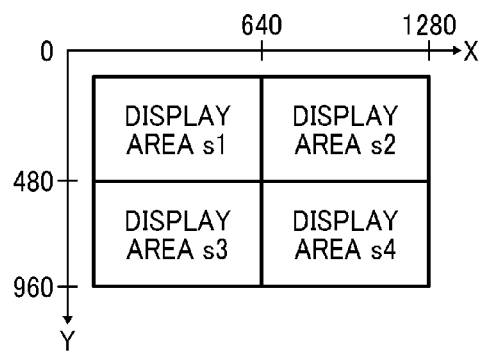
FIG. 9 is a conceptual diagram illustrating a sightline position management table as the embodiment of the present invention.
FIG. 10A is a conceptual diagram illustrating the calibration management table.
FIG. 10B is a conceptual diagram illustrating the display areas.

FIG. 9 is a conceptual diagram illustrating a sightline position management table. In this case, FIG. 9 illustrates a table used when the corneal reflex method is applied. The sightline position management table stores coordinate data indicating a position of the pupil against a position of the corneal reflex of a user eye, in association with display area information indicating a display area that includes a position of the user observing point on the display 217 of the communication terminals 10 and 40. The display area information indicates each of the four display areas s1, s2, s3, and s4 in the center part shown in FIG. 7B.

FIG. 10A is a conceptual diagram illustrating the calibration management table. FIG. 10B is a conceptual diagram illustrating the display areas. In FIG. 10B, the four display areas s1, s2, s3, and s4 in the center part in FIG. 7B are illustrated. In this example, it is assumed that the respective displays 217 in the communication terminals 10 and 40 have a size of 1280 pixels horizontally by 960 pixels vertically.

Figure 11:
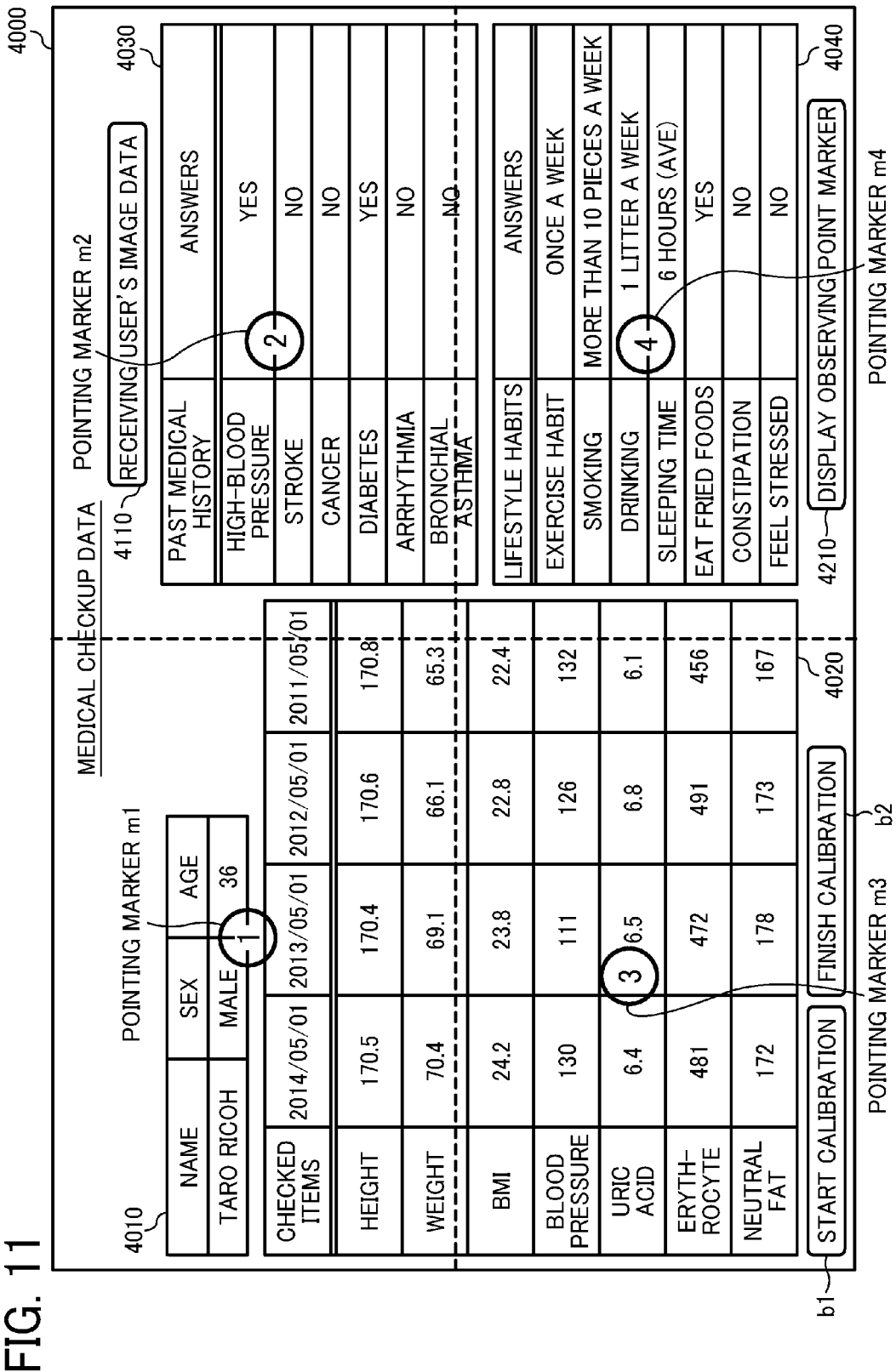
FIG. 11 is a diagram illustrating an industrial-physician-side screen indicating display positions of a pointing marker as the embodiment of the present invention.
Figure 12:
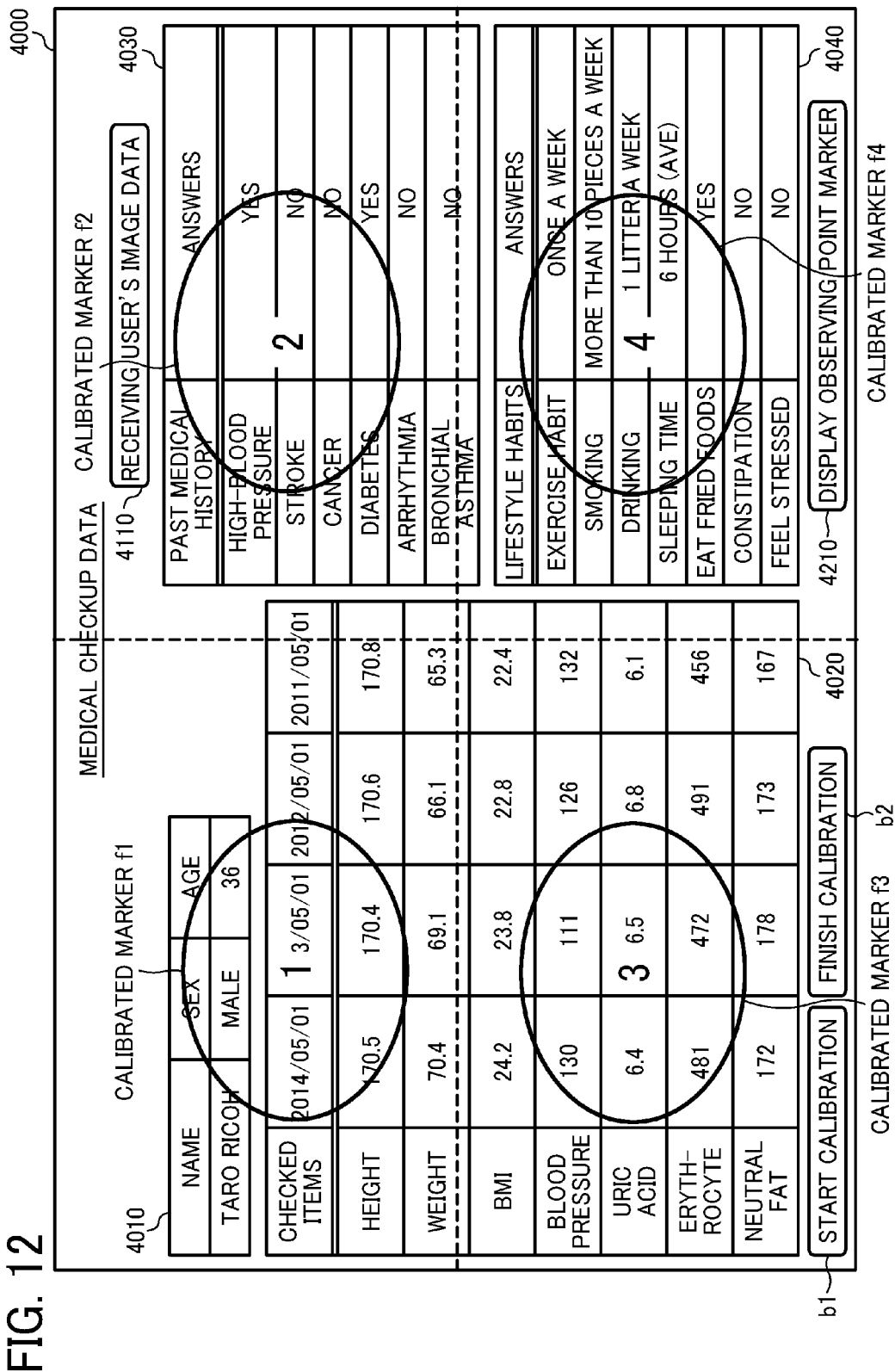
FIG. 12 is a diagram illustrating an industrial-physician-side screen indicating display positions of a calibrated marker as the embodiment of the present invention.
Figure 18:
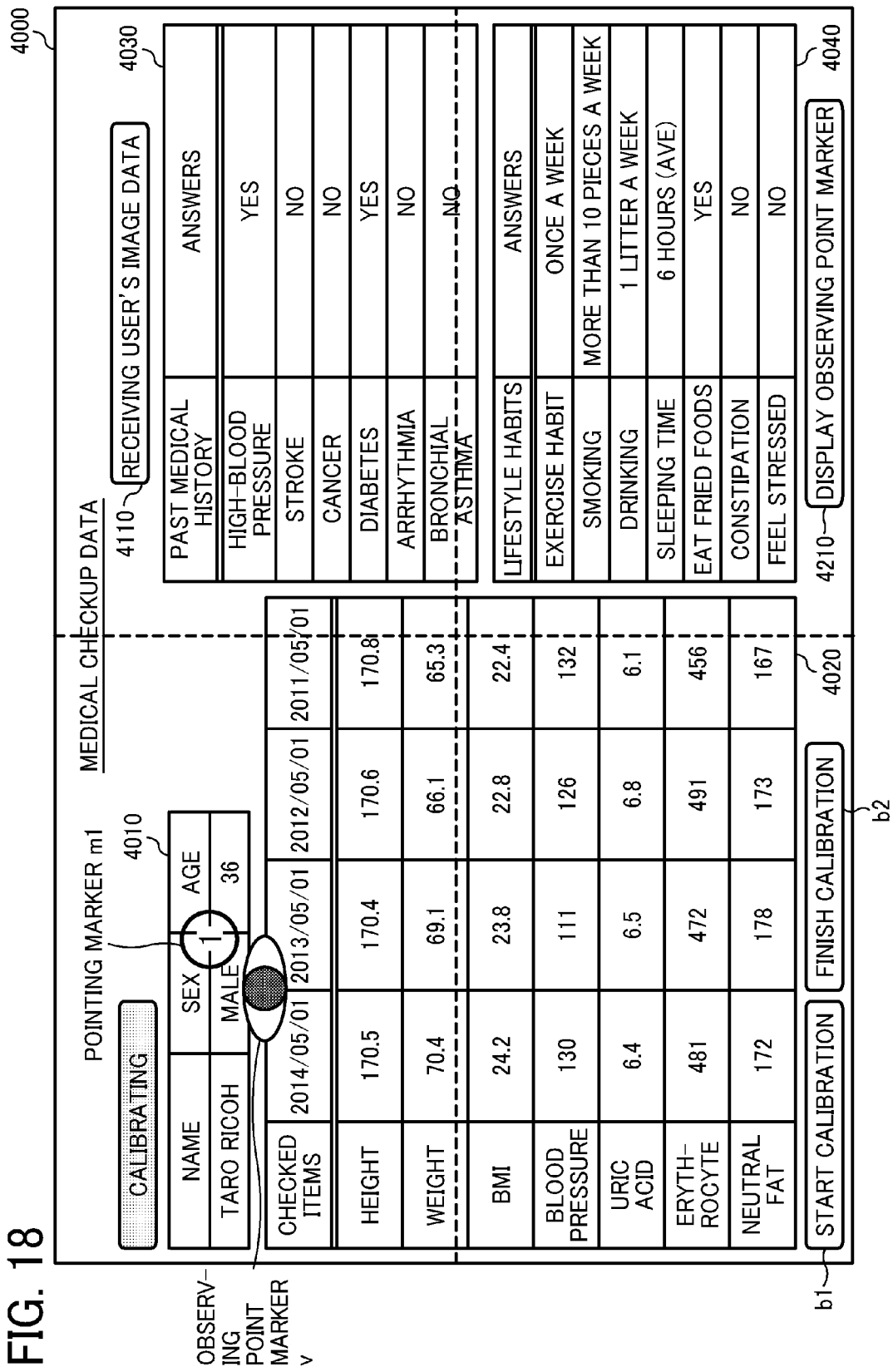
FIG. 18 is a diagram illustrating an industrial-physician-side screen during the calibration, according to an embodiment of the present invention.
Figure 19:
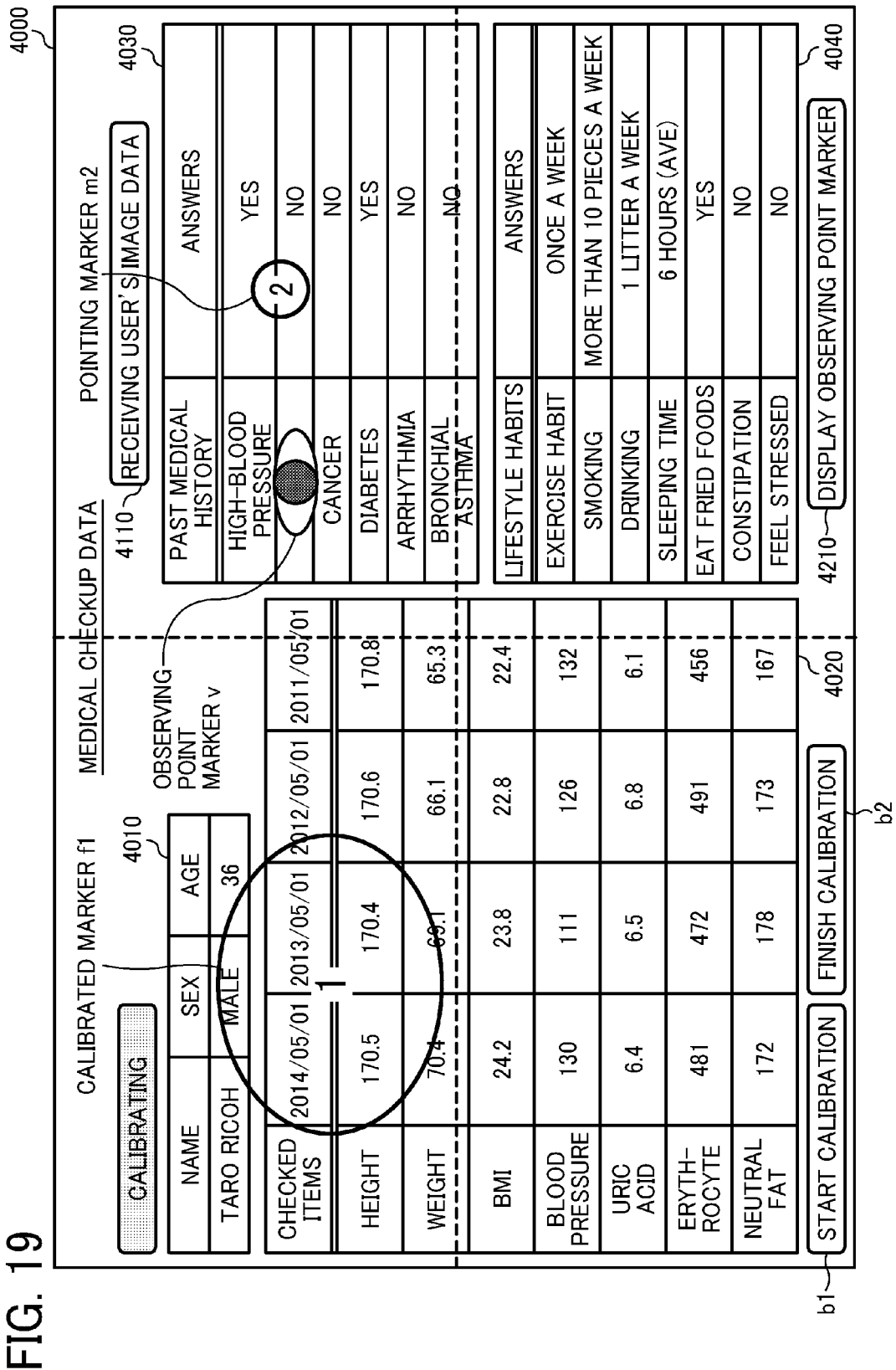
FIG. 19 is a diagram illustrating another industrial-physician-side screen during the calibration, according to an embodiment of the present invention.

FIG. 11 is a conceptual diagram illustrating display positions of pointing markers on the industrial-physician-side medical checkup data screen 4000. FIG. 12 is a conceptual diagram illustrating display positions of calibrated markers on the industrial-physician-side medical checkup data screen 4000. In FIGS. 11 and 12, dash lines that divide the screen into four parts are illustrated. Those dash lines visually represent the four display areas s1, s2, s3, and s4. Alternatively, the display controller 43 may not display the dash lines on the display 217. The case in which the dash lines are displayed is also illustrated in FIGS. 18 and 19 (described later).

Any one of the pointing markers m1, m2, m3, and m4 is referred to as "a pointing marker m" hereinafter. In addition, any one of the calibrated markers (standard markers to be used for calibration) f1, f2, f3, and f4 is referred to as "a calibrated marker f" hereinafter. In addition, the pointing marker m is an example of pointing information. Examples of displaying the pointing information other than displaying the marker include, but not limited to, modifying color of texts or width of frames etc. on the medical checkup data. Likewise, the calibrated marker f is an example of calibrated information. Other examples of the calibrated information include modifying color of texts or width of frames etc. on the medical checkup data.

Furthermore, on the lower left part of the medical checkup data screen 4000, "a start calibration button b1" to be pressed by the industrial physician to start calibration is displayed. In addition, "a finish calibration button b2" to be pressed by the industrial physician to finish the calibration is displayed.

The calibration management table of FIG. 10A stores, for each of the four display areas s1, s2, s3, and s4 in FIG. 10B, pointing position information indicating a display position of the pointing marker m, calibrated position information indicating a display position of the marker when the pointing marker is calibrated ("calibrated marker"), comparison result information indicating a comparison result obtained in the calibration process, and comparison status information indicating comparison status obtained in the calibration process associated with one another. Among them, as shown in FIG. 11, the display positions of the pointing markers are expressed as coordinate data for specifying the display positions of the pointing markers m1, m2, m3, and m4 in the respective display areas. Likewise, as shown in FIG. 12, the display positions of the calibrated markers are expressed as coordinate data for specifying the display positions of the calibrated markers f1, f2, f3, and f4 in the respective display areas.

The comparison result is a comparison result between the display area including the position of the pointing marker m and the display area including the employee's sightline position specified by the specification unit 45 in each one of the sixteen display areas shown in FIG. 7B. For example, it is assumed that the pointing marker m1 is displayed on the display area s1 and the employee's sightline position specified by the specification unit 45 is located within the hidden area h12. In that case, the display position of the pointing marker m1 obtained in the calibration process has a difference of "+1" area in the X-axis direction and a difference of "0" area in the Y-axis direction with respect to the employee's sightline position, such that the comparison result is considered as (+1, 0). That is, the employee's sightline position obtained in the calibration process has a difference of "−1" area in the X-axis direction and a difference of "0" area in the Y-axis direction against the display position of the pointing marker m1. In this example, signs of X-axis value and Y-axis value are inverted in the adjustment process to be later performed.

Furthermore, the comparison status indicates whether or not the employee's sightline position is compared with the display position of the pointing marker m in each of the display areas s1, s2, s3, and s4. The comparison status of "1" indicates that the comparison is finished. The comparison status of "0" indicates that the comparison is not finished.

In case of using the iris detection method or the AAM method, parameters are stored associated with the display area information instead of the coordinate data.

Next, the functional configuration of the communication terminal 40 is described below with reference to FIGS. 5 and 6, according to the embodiment of the present invention.

The transmission-reception unit 41 in the communication terminal 40 is mainly implemented by processes performed by the network I/F 210 and the CPU 201 shown in FIG. 5. Mainly, the transmission-reception unit 41 transfers various data to the communication terminal 10 or receives various data from the communication terminal 10 via the communication network 9.

The accepting unit 42 is mainly implemented by processes performed by the keyboard 208, the mouse 209, and the CPU 201 and accepts various selection, designation, or commands etc. by user operation.

The display controller 43 is mainly implemented by processes performed by the display I/F 218 and the CPU 201 and controls displaying various images and text on the display 217.

The determination unit 44 is mainly implemented by processes performed by the CPU 201 and determines whether or not the sightline data is received from the communication terminal 10.

The specification unit 45 is mainly implemented by processes performed by the CPU 201 and specifies the employee's observing point position on the display 217 of the communication terminal 40 based on the sightline data received by the transmission-reception unit 41 every time the transmission-reception unit 41 receives the sightline data.

The image processor 46 is mainly implemented by processes performed by the CPU 201 and superimposes the observing point marker v on the medical checkup data.

The communication unit 47 is mainly implemented by processes performed by the camera 212, the image capture device I/F 213, the microphone 214, the speaker 215, the audio input/output I/F 216, the display 217, the display I/F 218, and the CPU 201 and communicates audio and video to the counterpart communication terminal 10 to carry out communication between the communication terminals 10 and 40.

The calibration unit 48 generates calibration data indicating relationship between the employee's sightline position specified by the specification unit 45 that is obtained when displaying the pointing marker m on a predetermined position, and the predetermined position of the pointing marker m on the display 217 of the communication terminal 40 as a calibration result. More specifically, the calibration data indicates positional relationship between the first area including the sightline position specified by the specification unit 45 and the second area including the position of the pointing marker m on the display 217 of the communication terminal 40. For example, if the first area including the sightline position specified by the specification unit 45 is the same as the second area including the position of the pointing marker m on the display 217 of the communication terminal 40, the calibration unit 48 generates the calibration data indicating not to perform adjustment by the adjustment unit 51. By contrast, if the first area including the sightline position specified by the specification unit 45 is different from the second area including the position of the pointing marker m on the display 217 of the communication terminal 40, the calibration unit 48 generates the calibration data indicating to change the sightline position specified by the specification unit 45 so as to match the display area of the pointing marker m.

The storing/reading unit 49 stores various data in the storage unit 400 or reads various data from the storage unit 400.

The adjustment unity 51 adjusts the employee's sightline position specified by the specification unit 45 based on user calibration data managed by the user management table in FIG. 7A. For example, the adjustment unit 51 performs adjustment so that the marker representing the employee's sightline position is changed in display location from the first area (e.g., the hidden area h12) to the second area (e.g., the display area s1).

Figure 13:
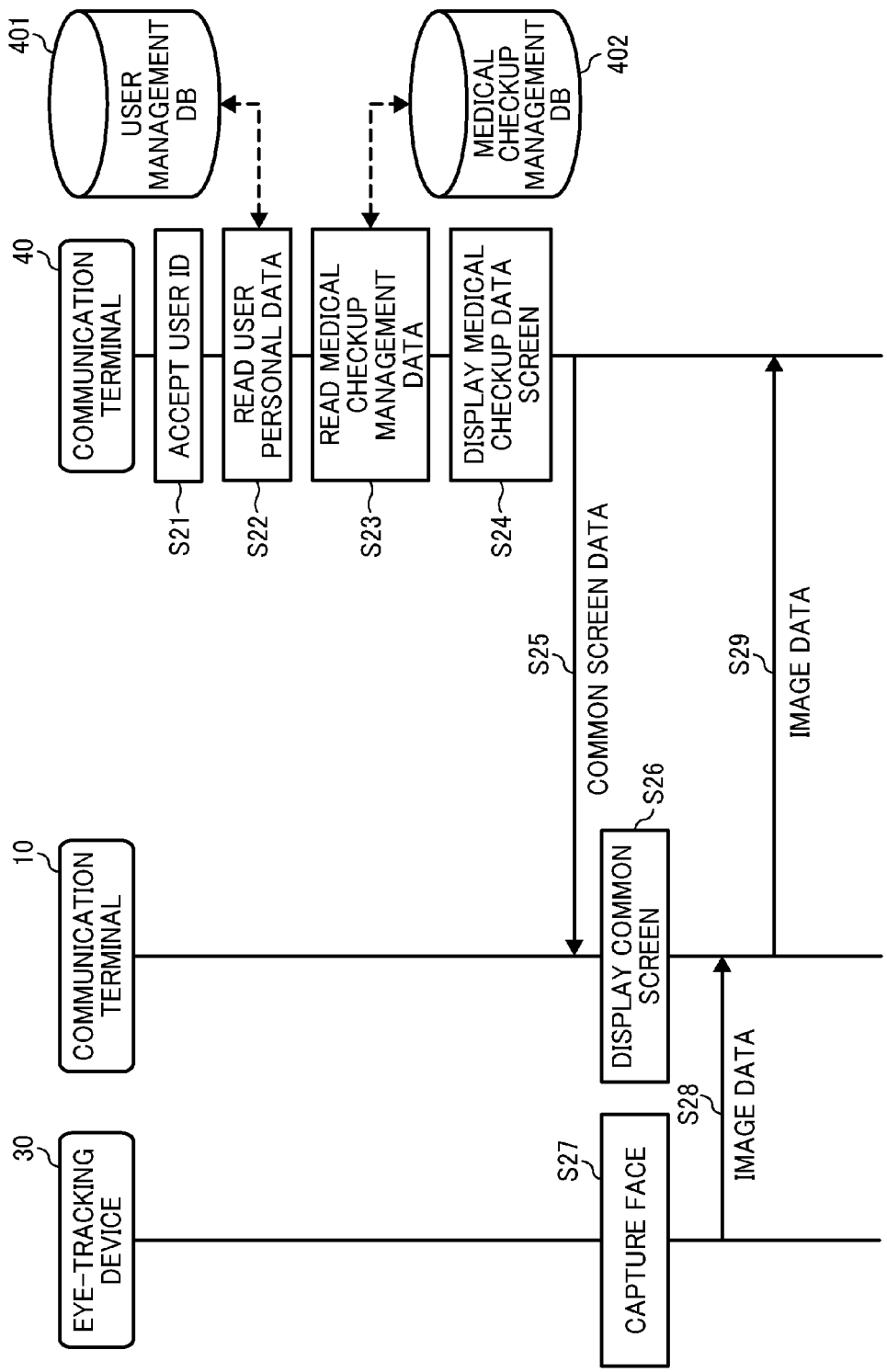
FIG. 13 is a sequence diagram illustrating operation of conducting a remote consultation, according to an embodiment of the present invention.
Figure 14:
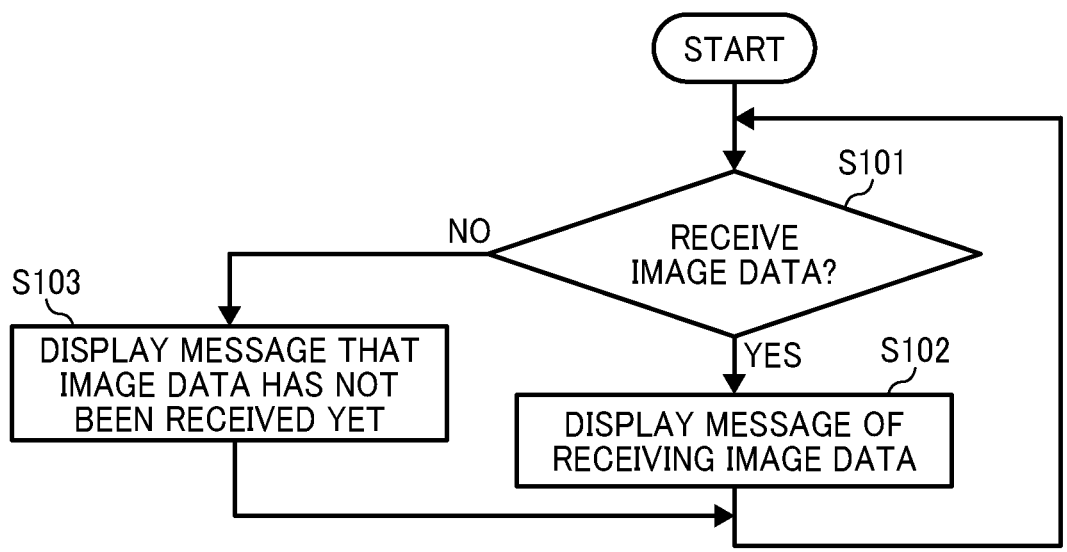
FIG. 14 is a flowchart illustrating operation of displaying a message on the industrial-physician-side screen, according to an embodiment of the present invention.
Figure 15:
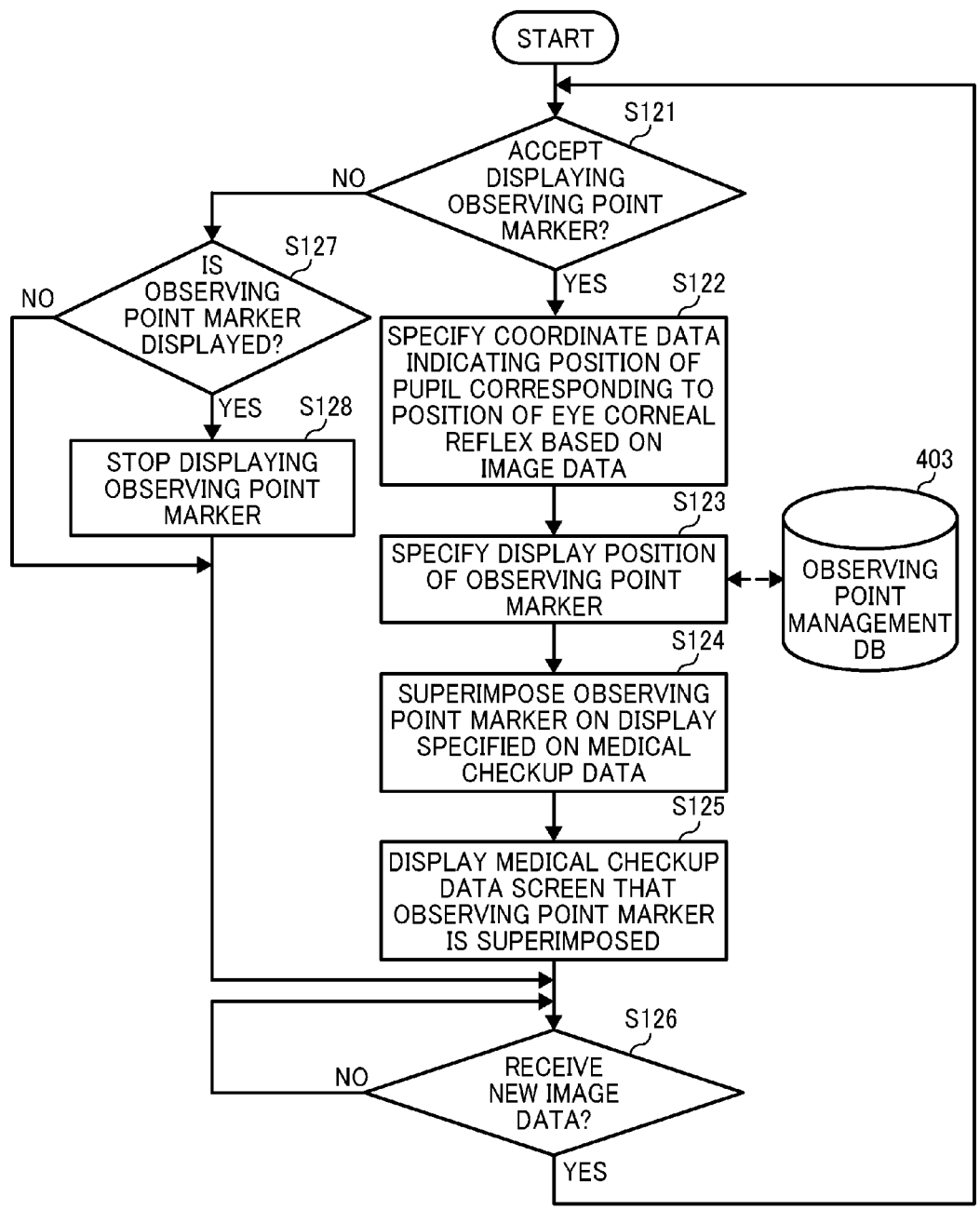
FIG. 15 is a flowchart illustrating operation of displaying an observing point marker on the industrial-physician-side screen, according to an embodiment of the present invention.

Next, processes and operations in this embodiment are described below with reference to FIGS. 13 to 15. FIG. 13 is a sequence diagram illustrating operation of carrying out a remote consultation. FIG. 14 is a flowchart illustrating operation of displaying a message on the industrial-physician-side screen. FIG. 15 is a flowchart illustrating operation of displaying the observing point marker on the industrial-physician-side screen.

First, just like the videoconference session, the employee and the industrial physician start the remote consultation using the communication terminals 10 and 40. At this point, the face of the user and at least a part of the room where the user resides at a counterpart site are displayed on the display 217 at a site where the user communicating with the counterpart user resides. As the industrial physician switches the current screen into an input screen and inputs the employee's user ID during the consultation, the accepting unit 42 receives input of the user ID in S21. Next, using the user ID accepted by the accepting unit 42 as a retrieval key, the storing/reading unit 49 searches through the user management table in the storage unit 400 (shown in FIG. 7) to read the user personal data indicating the corresponding user name, user sex, and user age for the user with the input user ID in S22. Furthermore, using the user ID accepted by the accepting unit 42 as the retrieval key, the storing/reading unit 49 searches through the medical checkup management table in the storage unit 400 (shown in FIG. 8) to read the medical checkup management data related to the corresponding user checkup items, user past medical history, and user lifestyle habits in S23. Subsequently, in the communication terminal 40, the display controller 43 displays the medical checkup data screen that consists of the user personal data and the medical checkup management data shown in FIG. 4 on the display 217 of the communication terminal 40 in S24. At this point, the observing point marker v and the message in the reception status display area 4110 have not been displayed yet.

Next, the transmission-reception unit 41 transfers shared screen data the same images as the display areas 4010, 4020, 4030, and 4040 to share the screen with the communication terminal 10 in S25. As a result, the transmission-reception unit 11 in the communication terminal 10 receives the shared screen data. Subsequently, in the communication terminal 10, the display controller 13 displays the medical checkup data screen shown in FIG. 3 on the display 217 of the communication terminal 10 in S26.

In addition, in the consultation room X, the lighting unit 31 in the sightline detection device 30 emits infrared light to the employee face, and the image capture unit 32 receives the reflected light to acquire the image data regarding the image including the employee eye in S27. The emission and reception operation are performed at a predetermined interval (e.g., every 0.5 seconds). Subsequently, the sightline detection device 30 transfers the image data from the connection unit 38 to the connection unit 18 in the communication terminal 10 in S28.

Next, the transmission-reception unit 11 in the communication terminal 10 transfers the image data to the communication terminal 40 via the communication network 9 in S29 As a result, the transmission-reception unit 41 in the communication terminal 40 receives the image data. The transmission/reception process of the image data described above is performed sequentially each time the sightline detection device 30 transfers the image data to the communication terminal 10 in S28.

Next, as shown in FIG. 14, in the communication terminal 40, the determination unit 44 determines whether or not the image data is received from the communication terminal 10 in S101. If the determination unit 44 determines that the sightline data is received (YES in S101), as shown in FIG. 4, the display controller 43 displays a receiving message indicating that the image data is being received in the reception status display area 4110 on the medical checkup data screen 4000 in S102. For example, as shown in FIG. 4, a message "receiving user's sightline data" is displayed as the receiving message. By contrast, if the determination unit 44 determines that the sightline data is not received from the communication terminal 10 (NO in S101), the display controller 43 displays a not-received message indicating that the sightline data has not been received yet in the reception status display area 4110 on the medical checkup data screen 4000 in S103. For example, a message "user's sightline data has not been received yet" is displayed as the not-received message. It should be noted that it is possible not to display a message if the image data has not been received.

Furthermore, as shown in FIG. 15, in the communication terminal 40, the determination unit 44 determines whether or not the accepting unit 42 accepts that the industrial physician requests to display the observing point marker v in S121. If the determination unit 44 determines that the request has been received (YES in S121), the specification unit 45 specifies coordinate data indicating a position of pupil against a position of corneal reflex of the eye based on the image data in S122. In addition, by searching through the sightline position management table in FIG. 9A using the coordinate data specified in S122 as the retrieval key, the specification unit 45 specifies a display position of the observing point marker v by reading corresponding display area information in S123.

Next, the image processor 46 superimposes the observing point marker v at the display position specified in S123 described above on the medical checkup data in S124. Subsequently, in the communication terminal 40, as shown in FIG. 4, the display controller 43 displays the medical checkup data screen 4000 on which the observing point marker v is imposed on the display 217 in the communication terminal 40 in S125.

After that, the determination unit 44 determines whether or not new image data is received in S126. Subsequently, in S126, if the determination unit 44 determines that the new image data is received (YES in S126), the process goes back to the step in S121. By contrast, in S126, if the determination unit 44 determines that the request has not been received yet (NO in S126), the determination unit 44 repeats the step in S126. For example, the repetition process is performed every one second.

By contrast, in S121, if the determination unit 44 determines that the request to display the observing point marker v has not been received yet (NO in S121), the determination unit 44 further determines whether or not the display controller 43 has already been displaying the observing point marker v in S127. If the determination unit 44 determines that the display controller 43 has already been displaying the observing point marker v (YES in S127), the display controller 43 stops displaying the observing point marker v in FIG. 4 in S128, and the process proceeds to S126. If the determination unit 44 determines that the display controller 43 is not displaying the observing point marker v (NO in S127), the process proceeds to S126. As shown in FIG. 4, if the observing point marker v is kept displaying on the medical checkup data screen 4000, the industrial physician might feel that it is difficult to recognize the medical checkup data screen 4000 in some cases. Therefore, it is possible to switch the observing point marker v from being displayed to not being displayed.

Figure 16:
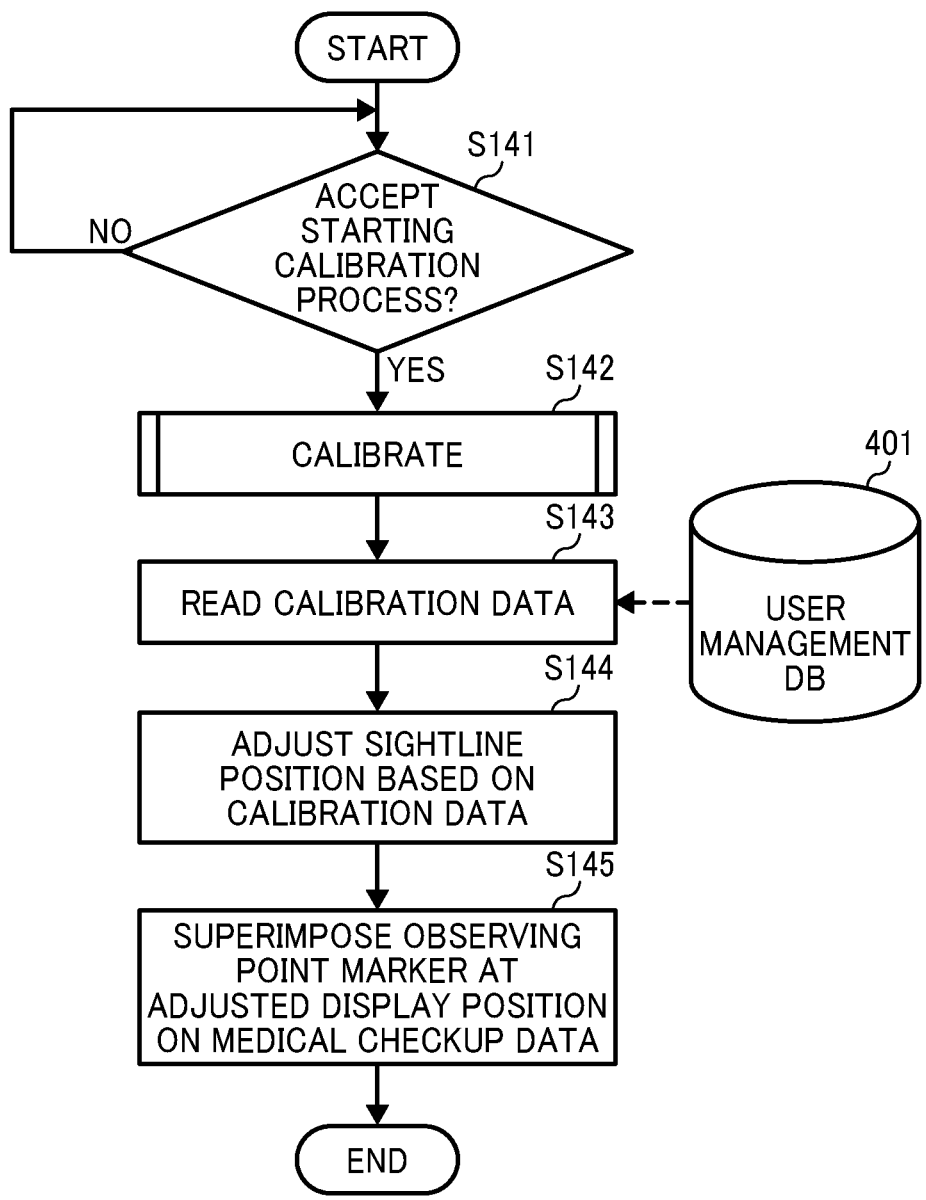
FIG. 16 is a flowchart illustrating operation of calibrating and adjusting a display position of an observing point marker, according to an embodiment of the present invention.

Next, the calibration process and the adjustment process of the display position of the observing point marker is described below with reference to FIGS. 16 to 19. FIG. 16 is a flowchart illustrating operation of calibrating and adjusting a display position of an observing point marker in this embodiment. The communication terminal 40 automatically starts/stops displaying in the order of the pointing marker m1, the calibrated marker f1, the pointing marker m2, the calibrated marker f2, the pointing marker m3, the calibrated marker f3, the pointing marker m4, and the calibrated marker f4. Since the same process of starting/stopping displaying is repeated, for simplicity, a process of starting displaying the pointing marker m1, stop displaying the pointing marker m1, starting displaying the calibrated marker f1, and starting displaying the pointing marker m2 is described below.

First, as shown in FIG. 16, the determination unit 44 in the communication terminal 40 determines whether or not the accepting unit 42 accepts the industrial physician's request to start the calibration process in S141. If the industrial physician presses the "start calibration" button b1 in FIG. 12, it is determined that the accepting unit 42 accepts starting the calibration process. As a result, the calibration unit 48 performs the calibration process in S142.

Figure 17:
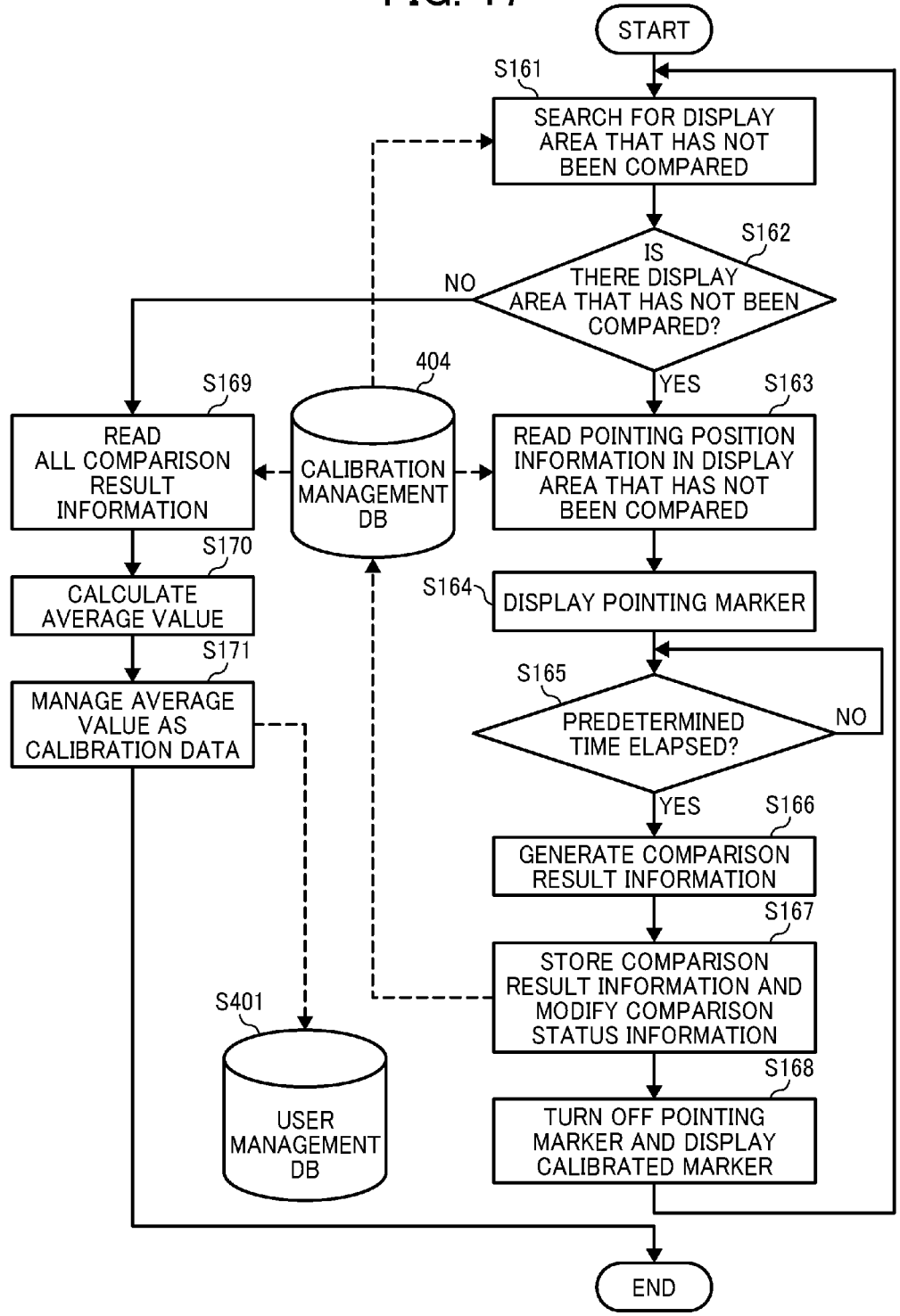
FIG. 17 is a flowchart illustrating operation of calibration, according to an embodiment of the present invention.

The calibration process is described below specifically with reference to FIGS. 17 to 19. FIG. 17 is a flowchart illustrating operation of calibration in this embodiment. FIGS. 18 and 19 are diagrams illustrating industrial-physician-side screens during the calibration in this embodiment. As shown in FIGS. 18 and 19, during the calibration process, the display controller 43 displays a message of "calibrating" indicating that the calibration process is performed in the upper left part of the industrial-physician-side medical checkup data screen.

As shown in FIG. 17, the storing/reading unit 49 searches for the display area indicating "0", i.e., indicating that the display area has not been compared yet, through the display area s1 to s4 in the calibration management table in FIG. 10A in S161. Subsequently, the determination unit 44 determines whether or not the display area that has not been compared yet exists in S162. If it is determined that the display area that has not been compared yet exists (YES in S162), the storing/reading unit 49 reads the pointing position information indicating the display position of the pointing marker in the display area that has not been compared yet in S163. Subsequently, for example, as shown in FIG. 18, the display controller 43 displays the pointing marker m1 on the medical checkup data screen 4000 based on the pointing position information in S164.

Accordingly, with reference to the display position of the pointing marker m1, the industrial physician prompts the employee to look at an item around the pointing marker m1 on the medical checkup data screen 4000 (e.g., "sex") via the communication. As a result, the employee points his/her sightline to the designated item on the medical checkup data screen 1000 (e.g., "sex").

Next, the determination unit 44 determines whether or not predetermined time elapses since the display controller 43 starts displaying the pointing marker m1 in S165. Subsequently, if it is determined that the predetermined time elapses (YES in S165), the calibration unit 48 generates the comparison result information at the display area s1 (e.g., "(+1, 0)") by comparing the display position of the pointing marker m1 with the employee's sightline position for that displayed position of the pointing marker m1 that is specified by the specification unit 45 after the predetermined time elapses in S166. After that, the storing/reading unit 49 stores the comparison result information generated in S166 in a recording part of the comparison result in a field of the display area s1 in the comparison management table in FIG. 10A. In addition, the storing/reading unit 49 changes the comparison status in the recording part of the comparison status in the field of the display area s1 from "not finished yet" to "finished" in S167.

Next, as shown in FIG. 19, the display controller 43 stops displaying the pointing marker m1 and starts displaying the calibrated marker f1 in S168. Subsequently, the process returns to S161.

By contrast, if it is determined that the display area that has not been displayed yet does not exist (NO in S162), the storing/reading unit 49 reads the comparison result information from all display areas, the first display area to the fourth display area, in the calibration management table in FIG. 10A in S169. Subsequently, the calibration unit 48 calculates an average value of sum of all comparison result information items in S170. For example, as shown in FIG. 10A, if the comparison result information is (+1, 0), (+1, 0), (0, 0), and (+1, 0), the average value becomes (+1, 0) after rounding off. Subsequently, the storing/reading unit 49 manages the average value as the calibration data in association with the user ID of the consulted employee in S171. As a result, the calibration process in S142 in FIG. 16 ends.

Next, using the user ID accepted in S21 described above as the retrieval key, the storing/reading unit 49 in the communication terminal 40 searches through the user management table (shown in FIG. 7A) to read the corresponding calibration data in S143. Subsequently, the adjustment unit 51 adjust the employee's sightline position specified by the specification unit 45 temporarily based on the calibration data in S144. For example, if the sightline position specified by the specification unit 45 is included in the hidden area h12 in FIG. 7B and the calibration data is (+1, 0), the adjustment unit 51 performs adjustment so that the sightline position is moved in display location from the hidden area h12 to the display area s1.

Next, the image processor 46 superimposes the observing point marker v at the display position adjusted in S144 described above on the medical checkup data in S145. Since the subsequent process is similar to the steps after S125 described above, its description is omitted.

As described above, by displaying the observing point marker v on the display 217 of the communication terminal 40 on the industrial physician's side, the industrial physician can carry out the remote consultation considering the employee's sightline just like the face-to-face consultation. By using the communication terminal in this embodiment described above, it is possible to carry out the remote interview with quality similar to the face-to-face interview.

For example, as shown in FIG. 4, in case of displaying the observing point marker v at a position different from the employee's name even if the industrial physician confirms the employee's name through the communication the industrial physician can recognize that the employee is in some kind of abnormal condition such as depression.

Especially, if positions where the observing point marker v vary frequently under the control of the display controller 43 based on the sightline data transferred from the communication terminal 10 sequentially, the industrial physician can further recognize that the employee is in abnormal condition more easily since the employee's sightline is unstable.

In addition, in displaying the observing point marker v of the user of the communication terminal 10 on the display 217 of the communication terminal 40, the communication terminal 40 can calibrate the display position of the observing point marker v via the communication network 2. As a result, in case of carrying out the remote interview, since it is possible to display the observing point marker v at a more precise position, the industrial physician can recognize that the employee is in some kind of abnormal condition more easily.

In the embodiment described above, the communication terminal 40 automatically starts/stops displaying the pointing marker m and the calibrated marker f. However, it is not limited to that, and the industrial physician can manually starts/stops displaying the pointing marker m and the calibrated marker f.

In the embodiment described above, the communication 40 displays the pointing marker m and the calibrated marker f during the calibration process. However, it is not limited to that, and it is possible to perform the calibration process automatically without displaying those markers.

Furthermore, in the embodiment described above, the calibration data calculated using the average value of the comparison result information. However, it is not limited to that. For example, it is possible to manage the comparison result information as is as the calibration data. In this case, in the user management table in FIG. 7, it is possible to allocate "a comparison result" field newly for storing/managing the comparison result information and the comparison result information is stored/managed using the table corresponding to the user ID. As a result, it is possible to perform the calibration process on each of the four display areas s1 to s4 using the corresponding comparison result information.

Numerous additional modifications and variations are possible in light of the above teachings. It is therefore to be understood that, within the scope of the appended claims, the disclosure of this patent specification may be practiced otherwise than as specifically described herein.

For example, while the above-described embodiment describes the case where an image of both eyes of the user is used to detect the user's sightline, at least one eye of the user may be captured as long as the user's sightline can be detected. For instance, if the user's dominant eye can be specified, the user's sightline may be detected using the image of the user's dominant eye.

As can be appreciated by those skilled in the computer arts, this invention may be implemented as convenient using a conventional general-purpose digital computer programmed according to the teachings of the present specification. Appropriate software coding can readily be prepared by skilled programmers based on the teachings of the present disclosure, as will be apparent to those skilled in the software arts. The present invention may also be implemented by the preparation of application-specific integrated circuits or by interconnecting an appropriate network of conventional component circuits, as will be readily apparent to those skilled in the relevant art.

Each of the functions of the described embodiments may be implemented by one or more processing circuits. A processing circuit includes a programmed processor. A processing circuit also includes devices such as an application specific integrated circuit (ASIC) and conventional circuit components arranged to perform the recited functions.

What is claimed is:

1. A communication terminal for communicating with a counterpart communication terminal, the communication terminal comprising:
   a receiver to receive image data, including an eye image representing an eye of a user operating the counterpart communication terminal, from the counterpart communication terminal, the eye image representing an eye of the user being captured but not displayed at the counterpart communication terminal while the user is viewing a position on a counterpart display; and
   circuitry to specify a sightline position indicating a sightline position of the user operating the counterpart communication terminal based on the received image data, generate calibration data indicating a relationship between a first area including the specified sightline position of the user and a second area including the position on the counterpart display, and adjust the specified sightline position of the user on a display at the communication terminal based on the generated calibration data.

2. The communication terminal of claim 1, wherein the counterpart display includes a plurality of display areas, and the circuitry is configured to compare a positional relationship between the first area including the specified sightline position of the user and the second area including the position on the counterpart display for each of the plurality of display areas of the counterpart display to generate a plurality of comparison results.

3. The communication terminal of claim 2, wherein the circuitry is configured to generate the calibration data based on an average value of the comparison results for the plurality of display areas.

4. The communication terminal of claim 1, wherein the circuitry is configured to control the display at the communication terminal to display sightline information indicating the sightline position of the user at the specified sightline position.

5. The communication terminal of claim 4, wherein the circuitry is configured to control the counterpart display at the counterpart communication terminal to display pointing information to guide the user to look at the position on the counterpart display, before receiving the eye image of the user at the counterpart communication terminal.

6. The communication terminal of claim 2, wherein the circuitry is configured to generate the calibration data indicating a relationship between the first area including the sightline position of the user and a second area including the position on the counterpart display for at least one of the plurality of display areas of the counterpart display, and is configured to display calibrated information indicating that the calibration data has been generated at the at least one of the plurality of display areas on the counterpart display when the calibration data is generated for the at least one of the plurality of display areas.

7. The communication terminal of claim 1, further comprising:
   a memory to store the generated calibration data,
   wherein the circuitry is configured to adjust the specified sightline position of the user based on the calibration data stored in the memory.

8. A system, comprising the communication terminal of claim 1.

9. A communication method, performed by a communication terminal in communication with a counterpart communication terminal, the method comprising:
   receiving image data including an eye image representing an eye of a user operating the counterpart communication terminal from the counterpart communication terminal, the eye image representing an eye of the user being captured but not displayed at the counterpart communication terminal while the user is viewing a position on a counterpart display;
   specifying a sightline position indicating a sightline position of the user operating the counterpart communication terminal based on the received image data;
   generating calibration data indicating a relationship between a first area including the specified sightline position of the user and a second area including the position on the counterpart display; and
   adjusting the specified sightline position of the user on a display at the communication terminal based on the generated calibration data.

10. The communication method of claim 9, further comprising controlling the display at the communication terminal to display sightline information indicating the sightline position of the user at the specified sightline position.

11. The communication method of claim 10, further comprising controlling the counterpart display at the counterpart communication terminal to display pointing information to guide the user to look at the position on the counterpart display, before receiving the eye image of the user at the counterpart communication terminal.

12. A non-transitory recording medium which, when executed by one or more processors of a communication terminal in communication with a counterpart communication terminal, cause the processors to perform a communication method, comprising:
   receiving image data including an eye image representing an eye of a user operating the counterpart communication terminal from the counterpart communication terminal, the eye image representing an eye of the user being captured but not displayed at the counterpart communication terminal while the user is viewing a position on a counterpart display;
   specifying a sightline position indicating a sightline position of the user operating the counterpart communication terminal based on the received image data;
   generating calibration data indicating a relationship between a first area including the specified sightline position of the user and a second area including the position on the counterpart display; and adjusting the specified sightline position of the user on a display at the communication terminal based on the generated calibration data.

13. The non-transitory recording medium of claim 12, to cause the processors to perform the communication method, further comprising controlling the display at the communication terminal to display sightline information indicating the sightline position of the user at the specified sightline position.

14. The non-transitory recording medium of claim 13, to cause the processors to perform the communication method, further comprising controlling the counterpart display at the counterpart communication terminal to display pointing information to guide the user to look at the position on the counterpart display, before receiving the eye image of the user at the counterpart communication terminal.

* * * * *